United States Patent
Thottathil

(10) Patent No.: US 10,449,190 B2
(45) Date of Patent: Oct. 22, 2019

(54) ALPHA-HYDROXY CARBOXYLIC ACID AND DERIVATIVES AND OTHER GRAS-BASED PRODRUGS OF OPIOIDS AND USES THEREOF

(71) Applicant: John K. Thottathil, Mundelein, IL (US)

(72) Inventor: John K. Thottathil, Mundelein, IL (US)

( * ) Notice: Subject to any disclaimer, the term of this patent is extended or adjusted under 35 U.S.C. 154(b) by 9 days.

(21) Appl. No.: 15/472,758

(22) Filed: Mar. 29, 2017

(65) Prior Publication Data

US 2017/0196851 A1 Jul. 13, 2017

Related U.S. Application Data

(63) Continuation-in-part of application No. 14/956,143, filed on Dec. 1, 2015, now Pat. No. 9,987,269, which is a continuation-in-part of application No. 14/953,392, filed on Nov. 29, 2015, now Pat. No. 10,017,519.

(60) Provisional application No. 62/153,157, filed on Apr. 27, 2015.

(51) Int. Cl.
*A61K 31/485* (2006.01)
*C07D 489/02* (2006.01)
*C07D 489/12* (2006.01)

(52) U.S. Cl.
CPC .......... *A61K 31/485* (2013.01); *C07D 489/02* (2013.01); *C07D 489/12* (2013.01)

(58) Field of Classification Search
CPC ... A61K 31/485; C07D 489/02; C07D 489/12
See application file for complete search history.

(56) References Cited

U.S. PATENT DOCUMENTS

| | | | |
|---|---|---|---|
| 4,673,679 A | 6/1987 | Aungst et al. | |
| 7,375,083 B2 | 5/2008 | Mickle et al. | |
| 8,759,368 B2 * | 6/2014 | Mickle | A61K 31/485 514/282 |
| 8,816,083 B2 | 8/2014 | Mickle et al. | |
| 9,987,269 B2 * | 6/2018 | Thottathil | A61K 31/485 |
| 10,017,519 B2 * | 7/2018 | Thottathil | C07D 489/08 |
| 10,226,456 B2 * | 3/2019 | Thottathil | C07D 489/08 |
| 2004/0058946 A1 | 3/2004 | Buchwald et al. | |
| 2005/0075361 A1 | 4/2005 | Wang | |
| 2005/0080012 A1 | 4/2005 | Mickle et al. | |
| 2007/0066537 A1 | 3/2007 | Mickle et al. | |
| 2008/0090771 A1 * | 4/2008 | Moncrief | C07D 489/02 514/18.3 |
| 2008/0207668 A1 * | 8/2008 | Moncrief | A61K 31/485 514/282 |
| 2010/0144645 A1 * | 6/2010 | Kirk | A61K 9/0019 514/1.1 |
| 2010/0286186 A1 | 11/2010 | Franklin et al. | |
| 2011/0040072 A1 | 2/2011 | Mickle et al. | |
| 2011/0053971 A1 | 3/2011 | Guillaume et al. | |
| 2013/0079364 A1 * | 3/2013 | Jenkins | A61K 31/4748 514/282 |
| 2014/0200235 A1 | 7/2014 | Riggs-Sauthier et al. | |
| 2016/0326182 A1 | 11/2016 | Peltier et al. | |

FOREIGN PATENT DOCUMENTS

| | | |
|---|---|---|
| WO | 03/032990 A2 | 4/2003 |
| WO | 03/072046 A2 | 9/2003 |
| WO | 2004082620 A2 | 9/2004 |
| WO | 2007/120648 A2 | 10/2007 |
| WO | 2007120864 A2 | 10/2007 |
| WO | 2010/112942 A1 | 10/2010 |
| WO | 2017091827 A1 | 6/2017 |
| WO | 2017095734 A1 | 6/2017 |

OTHER PUBLICATIONS

Final Office Action in U.S. Appl. No. 14/956,143, dated Jul. 17, 2017, 18 pages.
Final Office Action in U.S. Appl. No. 15/139,836, dated Jul. 6, 2017, 16 pages.
Final Office Action in U.S. Appl. No. 14/953,392, dated Oct. 19, 2017, 14 pages.
Non-Final Office Action in U.S. Appl. No. 14/956,143 dated Dec. 28, 2016, 12 pages.
Non-Final Office Action in U.S. Appl. No. 14/953,392 dated Jan. 13, 2017, 15 pages.
PCT International Search Report and Written Opinion in PCT/US16/63834 dated Jan. 31, 2017, 17 pages.
PCT International Search Report and Written Opinion in PCT/US16/63836 dated Jan. 24, 2017, 17 pages.
Aquina, C.T., et al., "OxyContin Abuse and Overdose", Postgrad Med. vol. 121, Issue 2, Mar. 2009, 163-67.
International Search Report and Written Opinion in Int. Appln. No. PCT/US18/24476, dated May 17, 2018, 24 pages.
Final Office Action in U.S. Appl. No. 15/139,836, dated Oct. 10, 2018, 10 pages.
PCT International Preliminary Report on Patentability in Intl. Appln. No. PCT/US2016/063836, dated Jun. 14, 2018, 10 pages.
"PCT International Preliminary Report on Patentability in PCT/US2016/063834 dated Jun. 7, 2018, 10 pages".
Non-Final Office Action in U.S. Appl. No. 15/955,968 dated Mar. 22, 2019, 38 pages.

* cited by examiner

Primary Examiner — My-Chau T. Tran
(74) Attorney, Agent, or Firm — Servilla Whitney LLC

(57) ABSTRACT

The invention describes pharmaceutical compounds and compositions comprised of a ligand attached to opioids in a manner that substantially decreases or deters the potential for opioid abuse, addiction, illicit and illegal use, and overdose. When delivered at the proper dosage, the pharmaceutical composition provides therapeutic activity similar to that of the parent active agent.

12 Claims, No Drawings

ALPHA-HYDROXY CARBOXYLIC ACID AND DERIVATIVES AND OTHER GRAS-BASED PRODRUGS OF OPIOIDS AND USES THEREOF

CROSS REFERENCE TO RELATED APPLICATIONS

This is a continuation-in-part of pending U.S. patent application Ser. No. 14/953,392, filed Nov. 29, 2015, and a continuation-in-part of pending U.S. patent application Ser. No. 14/956,143, filed Dec. 1, 2015, the disclosures of which are incorporated by reference in their entireties. U.S. patent application Ser. No. 14/953,392 and U.S. patent application Ser. No. 14/956,143 each claim the benefit of U.S. Provisional Application No. 62/153,157, filed on Apr. 27, 2015.

FIELD OF INVENTION

The present invention relates to pharmaceutical compounds, compositions, and methods of using chemical moieties that are generally recognized as safe (GRAS), which are attached to the opioid (e.g. hydrocodone, hydromorphone, morphine, codeine, dihydrocodeine, buprenorphine, oxycodone, oxymorphone) molecules. These chemical moieties are monomers, homo- and hetero-oligomers, of alpha-hydroxy carboxylic acids and their chemical derivatives. These inventions provide a variety of beneficial effects, particularly a substantial decrease in the potential of opioids to cause overdose or to be abused. Some embodiments of the invention provide therapeutic activity similar to that of unmodified opioid at typical dosage ranges; but when delivered at higher doses, the potential for overdose is reduced due to decreased bioavailability of the opioid, especially when taken by non-approved routes, as compared to the opioid that is administered by the approved oral route and delivered in a non-conjugated form. Additionally, these prodrugs may be designed to provide fast or slow release of opioid depending on its standard use for chronic or acute pain.

BACKGROUND OF THE INVENTION

Proper medical treatment of pain remains a challenge for patients and healthcare professionals. Optimal pharmacologic management of pain requires selection of analgesic drugs that achieve rapid efficacy with minimal side effects. Traditionally, opioid analgesics have provided the most important options for pain treatment. However, misuse and abuse of opioids are widespread social and medical problems that may deter physicians from prescribing these useful drugs.

In addition, accidental and intentional overdose with prescription and/or over-the-counter (OTC) drugs is a serious health problem that is associated with thousands of fatalities every year. Opioid overdose is a significant and growing problem associated with drug abuse, but overdoses also occur accidentally (e.g., when a child obtains and ingests an opioid drug, say Oxycontin® or Opana® or Vicodin®), or intentionally (e.g., when related to suicide attempts). Accidental overdose can also commonly occur when unusually potent batches of illicit opioids are ingested by drug addicts or other abusers.

Opioid abuse is an increasing problem, and opioids have become one of the most widely abused drugs. The opioid drug is also known as "a poor man's heroin" because of its comparatively lower street price. Moreover, crushing and snorting intranasally the delayed release form of oxycodone (known by the brand name as Oxycontin®), results in rapid drug release and absorption, which results in high peak blood concentrations that produce a quick "high" but can also precipitate a fatal overdose (Aquina et al (2009) Post Graduate Medicine 121: 163-167). Necrosis of intranasal structures, similar to the damage associated with cocaine use, is also a consequence of prolonged Oxycontin® abuse by snorting crushed tablets. Moreover, crushing and intranasally snorting the extended release form of oxymorphone (known by the brand name as Opana-ER®), results in rapid drug release and absorption, causing high peak blood concentrations that produce a quick "high" but can also precipitate a fatal overdose. Moreover, in March 2015, Austin, Ind. was the center of an HIV outbreak caused by the use of opioids as an injectable recreational drug. Opioids such as Opana® have various street names, such as "blues", "moons", "blue heaven", "pink lady", "Mrs. O", and others.

A further shortcoming of many opioids is their generally low oral bioavailability. Poor oral bioavailability results in variable blood levels, and consequently variable patient response—a highly undesirable feature in the treatment of pain where rapid and reliable relief is critical.

Researchers and the pharmaceutical industry have sought to prevent the potential harmful effects of opioid overdose by creation of various drug formulations. For example, opioids have been combined with opioid antagonists. Such formulations are designed to counteract an oral opioid if the formulation is disrupted (e.g., crushed) prior to oral administration, or if the drug is taken administered parenterally (e.g., injected intravenously). To cite an example of a non-opioid drug with known abuse potential, extended-release methylphenidate (Concerta®) has been formulated in a paste that can preclude administration by snorting or injection. Another example is the drug Embeda® where the opioid drug morphine is co-formulated with the antagonist naltrexone in sequestered fashion. Other compositions have been coated with emetic agents in quantities that—if administered in moderation as intended—no emesis occurs; however, if excessive amounts are ingested, emesis is induced to prevent overdose. However, such methods, as well as conventional controlled-release formulations, are often ineffective and can be circumvented.

In addition to oxymorphone hydrochloride, oxymorphone is also an ingredient of Opana® Injection (injectable), Opana® ER (extended-release tablet), Opana® IR (immediate-release tablet), Numorphan® (suppository and injectable solution), and O-Morphon® (both tablet and injectable). It is a semi synthetic narcotic analgesic derived from thebaine. Typical adult doses of opioid range from 5-40 mg as the oral hydrochloride salt, whereas the injectable adult dose is approximately 1 mg as the hydrochloride salt, with a dosing interval ranging from 4-12 hours.

In addition to Oxycontin®, oxycodone is also an ingredient of well-known drugs such as Percodan®, Percocet®, Roxicet®, and Tylox®. As a semi-synthetic narcotic derived from thebaine, oxycodone is also available in oral formulations combined with aspirin, phenacetin, and caffeine. A typical adult dose of oxycodone is 2.5-5 mg administered orally as the hydrochloride or terephthalate salt every 6 hours. While typically used for the relief of moderate to moderately severe pain, opioid can also produce drug dependence of the morphine type.

In the case of hydrocodone, there are several FDA approved products in the market, but most of them are combination products, mainly co-formulated with acetaminophen. In addition to Vicodin®, hydrocodone is also an ingredient of well-known drugs such as Hy-Phen®, Co-Gesic®, Hycodan®, Codamine®, Hysingla®, Lortab®, Lorcet-HD®, Norcet®, Vicoprin®, Zohydro ER®, Zydone® etc. to mention a few.

Various types of prodrugs have been proposed to improve the oral bioavailability of opioids. These have included simple ester conjugates that are subject to hydrolysis by plasma esterases. Moreover, the rapidity of ester hydrolysis within the gut or through first-pass metabolism in the liver has further limited the utility of this approach. More sophisticated ester-conjugated opioid prodrugs have been synthesized. However, in the 20 years since ester conjugates were first reported, no such prodrugs have been approved as marketed products, which suggests that this approach has not been successful.

Consequently, improved methods are urgently needed to make pharmaceutically effective opioid compounds, along with compositions and methods of using such compounds, to reduce the potential for overdose and to reduce or deter opioid substance abuse while maintaining intended analgesic utility. Potentially useful compounds may also prevent—or substantially diminish or delay—uptake into the brain if the compounds were administered by routes other than approved oral administration.

Ideally, a prodrug moiety and its linkage to a particular opioid would be cleaved at an appropriate rate and site, which would then release the active opioid compound into the blood and provide the intended analgesic benefit. There remains a critical need for the treatment of severe pain with opioids using products that retain all their pharmacological advantages but sharply reduce their principal limitations, including adverse gastrointestinal effects (e.g., constipation), variable bioavailability after oral dosing, opioid overdose, and misuse, illegal/illicit use and product tampering.

SUMMARY

Provided are pharmaceutical compounds, compositions, and methods of using such compounds and compositions. Also provided are methods of using chemical moieties that are generally recognized as safe (GRAS), which are attached to the opioid molecule. These chemical moieties are monomers, homo- and hetero-oligomers of alpha-hydroxy carboxylic acids, and their chemical derivatives. The compounds may provide a substantial decrease in the potential of opioid to cause overdose or to be abused. In some embodiments the opioid prodrug conjugates provide therapeutic activity which is similar to that of unmodified parent drug when delivered at typical dosage ranges. However, when delivered at higher doses the potential for overdose is reduced as compared to conventional non-conjugated opioid due to decreased bioavailability of the opioid, especially when taken by non-approved oral routes. Additionally, the prodrugs may be designed to provide fast or slow release of the opioid depending on its standard use for chronic or acute pain. The drugs/molecules that are covered in this invention include all the opioid drugs including but not limited to; Oxycodone, Hydrocodone, Oxymorphone, Hydromorphone, Morphine, Codeine, Dihydrocodeine, and Buprenorphine.

DETAILED DESCRIPTION OF THE INVENTION

A first aspect of the invention relates to changing the pharmacokinetic and pharmacological properties of opioid drugs through covalent modification of opioids using alpha-hydroxy carboxylic acid and derivatives and other generally recognized as safe (GRAS)-based moieties to produce prodrugs of opioids. Covalent attachment of a chemical moiety—specifically, a moiety derived from alpha-hydroxy carboxylic acid and derivatives, as well as other GRAS-based reagents as monomers and oligomers (homo and hetero oligomers)—to opioids may change one or more of the following properties of opioids: the rate of absorption; extent of absorption and distribution within the body; metabolism and drug elimination (i.e., ADME pharmacokinetic properties). As such, the alteration of one or more of these characteristics may be designed to provide fast or slow release, depending on need for relief of chronic pain versus acute pain. Additionally, alteration of one or more of these characteristics may reduce the previously noted side-effects associated with opioids. In turn, these alterations may diminish or deter abuse potential. The oligomers formed from alpha-hydroxy carboxylic acid and derivatives can be homo- and hetero-'mers' and can be both linear and branched 'mers'. The hetero 'mers' can be cross linked with other GRAS reagents. such as other alpha-hydroxy carboxylic acid, amino acid and dicarboxylic acids including, but not limited to, fumaric acid, maleic acid and succinic acid.

The opioid prodrugs may also prevent abuse by exhibiting stability under conditions that are likely to be employed by chemists who may illicitly attempt to release the opioid compound from its attached group. The opioid prodrugs may further prevent abuse by exhibiting reduced bioavailability when administered via parenteral routes, particularly by intravenous, intranasal, or inhalation ("smoking") routes that are often employed in illicit use. Thus, the opioid prodrugs may reduce the desired euphoric effect associated with opioid abuse, thereby preventing, deterring, or reducing abuse potential and overdose if the opioid prodrugs were to be used in an unapproved manner (e.g., ingestion of a higher dose or by non-oral administration).

Opioid prodrugs of the present invention may be depicted as the structure shown below where "OP" represents the opioid and "X" represent the prodrug component that is chemically/covalently attached to the opioid "OP".

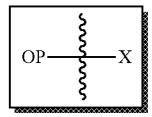

Specifically, opioid prodrugs of the present invention may be depicted as structures shown as Formula A-Formula F where moiety X represents the prodrug component. Formula A is the hydrocodone prodrug in which the prodrug moiety X is chemically/covalently attached to hydrocodone at the $6^{th}$ position oxygen atom of hydrocodone as its ketone enolate ester. Formula B is the hydromorphone prodrug in which the prodrug moiety X is chemically/covalently attached to hydromorphone at the $6^{th}$ position oxygen atom of hydromorphone as its ketone enolate ester. Formula C is the morphine prodrug in which the prodrug moiety X is chemically/covalently attached to morphine at the $6^{th}$ position oxygen atom of morphine as its alcohol ester. Formula D is the codeine prodrug in which the prodrug moiety X is chemically/covalently attached to codeine at the $6^{th}$ position oxygen atom of codeine as its alcohol ester. Formula E is the dihydrocodeine prodrug in which the prodrug moiety X is chemically/covalently attached to dihydrocodeine at the $6^{th}$ position oxygen atom of dihydrocodeine as its alcohol ester.

Formula F is the buprenorphine prodrug in which the prodrug moiety X is chemically/covalently attached to buprenorphine at the side chain alcohol oxygen atom of buprenorphine as its alcohol ester. As shown in Formula F, the side chain is attached to position 7 of the core ring and the alcohol group is at position 17 of the side chain. The opioid prodrugs of the present invention depicted as Formula A-Formula F can also be represented as their pharmaceutically acceptable salts.

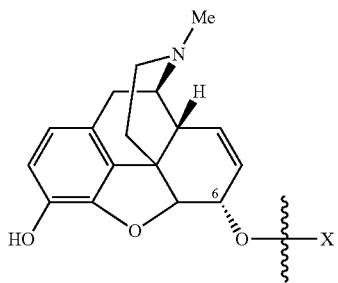

Hydrocodone    Hydromorphone

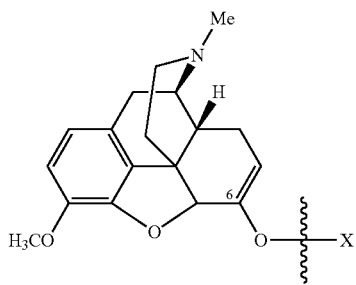

Morphine (Formula A)

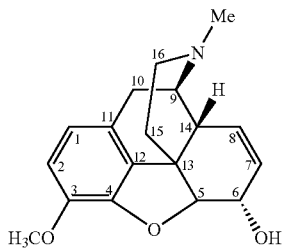

Hydrocodone prodrug (Formula B)

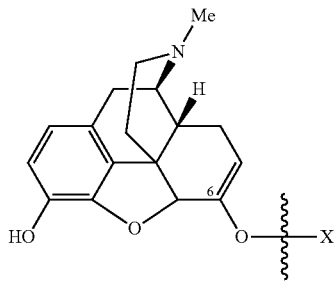

Hydromorphone prodrug (Formula C)

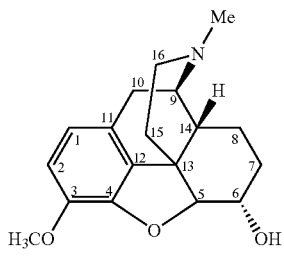

Morphine prodrug

Codeine

Dihydrocoedine

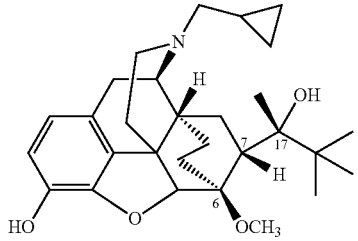

Buprenorphine (Formula D)

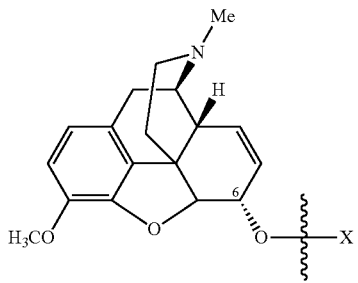

Codeine prodrug

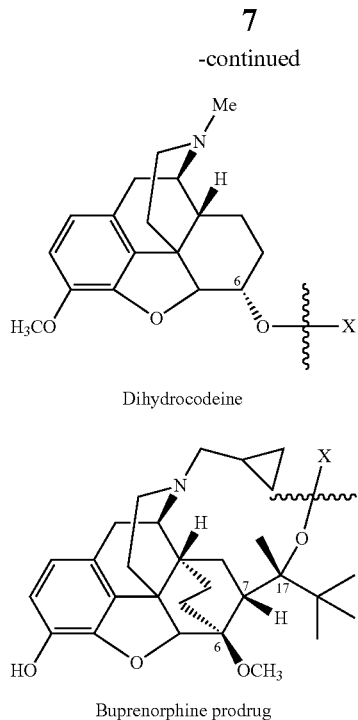

Dihydrocodeine

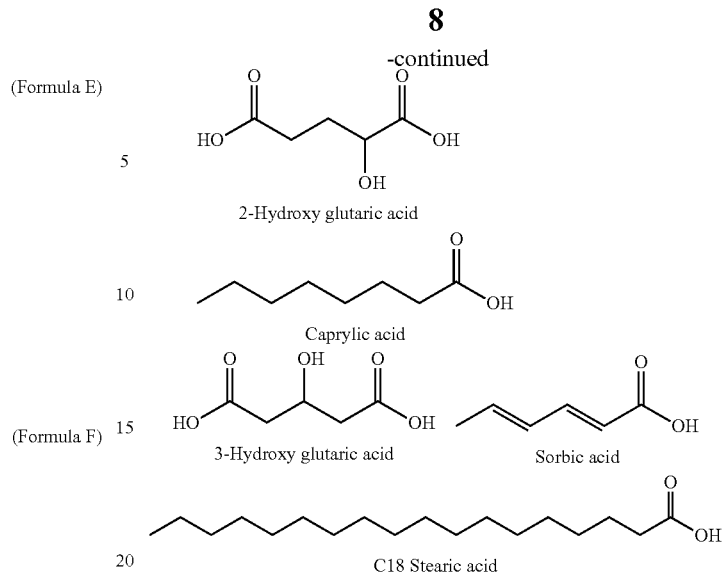

2-Hydroxy glutaric acid

Caprylic acid

3-Hydroxy glutaric acid    Sorbic acid

C18 Stearic acid

Buprenorphine prodrug

Alpha-hydroxy carboxylic acids and other GRAS-based monomers used to make the monomer-based and oligomer-based opioid prodrugs are depicted below.

It should be emphasized that the following chemical moieties represent non-limiting examples of alpha-hydroxy carboxylic acids and other GRAS-based monomers used to make the monomer-based and oligomer-based opioid prodrugs of the present invention:

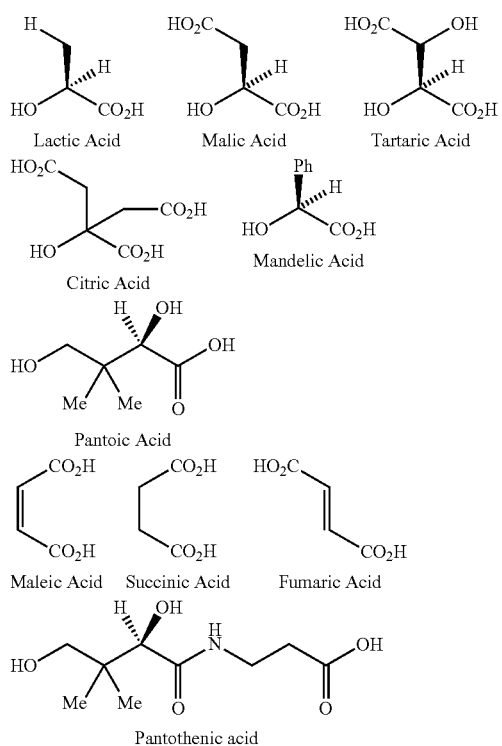

C8-C20 Fatty Acids; Palmitic Acid, Linoleic Acid, Oleic Acid as Examples

Amino Acids Including Alpha, Beta, Gamma and Epsilon Amino Acids

The alpha-hydroxy carboxylic acids represented here include the naturally occurring (L)-isomers, the non-natural (D)-isomers, mixtures of (L) and (D) isomers, racemates and mixtures of diastereomers, and meso-isomers.

The amino acids represented here include both natural and non-natural amino acids, the naturally occurring (L)-isomers, the non-natural (D)-isomers, mixtures of (L) and (D) isomers, racemates and mixtures of diastereomers.

The amino acids represented here also include alpha amino acids, beta amino acids, gamma amino acids, and epsilon amino acids (i.e., amino group remote relative to the carboxyl group).

The fatty acids represented here include long-chain carboxylic acids, ranging in carbon lengths between eight carbons (C8) to twenty carbons (C20). These fatty acids could be both linear and branched and both saturated and non-saturated. In the case of unsaturated fatty acids, they could be both cis- and trans-isomers (Z and E isomers).

In one embodiment of the present invention, the prodrug component X may be represented as,

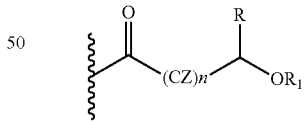

wherein,
CZ=CH2, or CHOR1,
R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and,
R=Methyl (Me), Phenyl (Ph), CH2COR2, CHOR1COR2, or COR2 (when n is not zero), where R2=OH, an ester formed by the hydroxyl group of another alpha-hydroxy acid or an amide formed by the amine group of an amino acid, and,
n is an integer selected from 0 to 2.

In another embodiment of the present invention, the prodrug component X may be represented as,

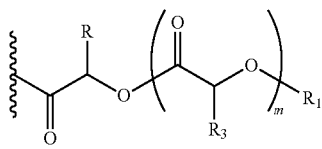

wherein,

R1=H, an acyl linkage of a fatty acid, an acyl linkage of an alpha-hydroxy acid, an acyl linkage of an amino acid or an acyl linkage of a dicarboxylic acid including, but not limited to, fumaric acid, maleic acid and succinic acid, and, R and R3 can be same or different, and, R and R3=Me, Ph, CH2COR2, or CHOR1COR2, where R2=OH or is an ester formed by the hydroxyl group of another alpha-hydroxy acid or is an amide formed by the amine group of an amino acid, and, m is an integer selected from 0 to 4.

In another embodiment of the present invention, the prodrug component X may be represented as,

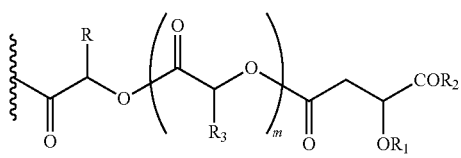

wherein,

R1=H, an acyl linkage of a fatty acid, an acyl linkage of an alpha-hydroxy acid, an acyl linkage of an amino acid or an acyl linkage of a dicarboxylic acid including, but not limited to, fumaric acid, maleic acid and succinic acid, and, R and R3 can be same or different, and, R and R3=Me, Ph, CH2COR2, or CHOR1COR2, where R2=OH or is an ester formed by the hydroxyl group of another alpha-hydroxy acid or is an amide formed by the amine group of an amino acid, and, m is an integer selected from 0 to 4.

In another embodiment of the present invention, the prodrug component X may be represented as,

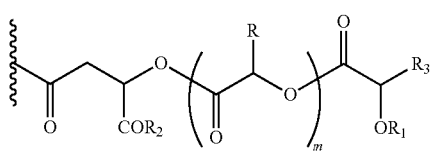

wherein,

R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and, R and R3 can be same or different, and, R and R3=Me, Ph, CH2COR2, or CHOR1COR2, where R2=OH or is an ester formed by the hydroxyl group of another alpha-hydroxy acid or is an amide formed by the amine group of an amino acid, and, m is an integer selected from 0 to 4.

In another embodiment of the present invention, the prodrug component X may be represented as,

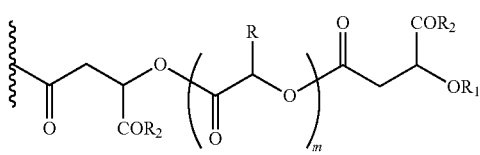

wherein,

R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and, R=Me, Ph, CH2COR2, or CHOR1COR2, where R2=OH or is an ester formed by the hydroxyl group of another alpha-hydroxy acid or is an amide formed by the amine group of an amino acid, and, m is an integer selected from 0 to 4.

In another embodiment of the present invention, the prodrug component X may be represented as,

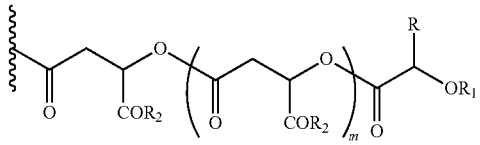

wherein,

R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and, R=Me, Ph, CH2COR2, or CHOR1COR2, where R2=OH or is an ester formed by the hydroxyl group of another alpha-hydroxy acid or is an amide formed by the amine group of an amino acid, and, m is an integer selected from 0 to 4.

In another embodiment of the present invention, the prodrug component X may be represented as,

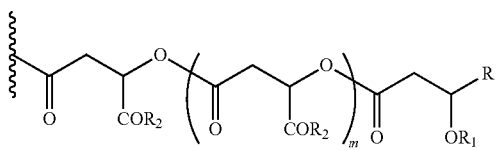

wherein,

R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and, R=Me, Ph, CH2COR2, or CHOR1COR2, where R2=OH or is an ester formed by the hydroxyl group of another alpha-hydroxy acid or is an amide formed by the amine group of an amino acid, and, m is an integer selected from 0 to 4.

In another embodiment of the present invention, the prodrug component X may be represented as,

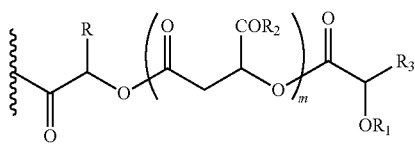

wherein,
R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid and,
R and R3 can be same or different, and,
R and R3=Me, Ph, CH2COR2, or CHOR1COR2, where R2=OH or is an ester formed by the hydroxyl group of another alpha-hydroxy acid or is an amide formed by the amine group of an amino acid, and,
m is an integer selected from 0 to 4.

In another embodiment of the present invention, the prodrug component X may be represented as,

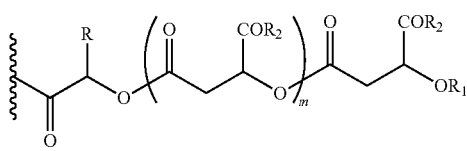

wherein,
R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and,
R=Me, Ph, CH2COR2, or CHOR1COR2, where R2=OH or is an ester formed by the hydroxyl group of another alpha-hydroxy acid or is an amide formed by the amine group of an amino acid, and,
m is an integer selected from 0 to 4

In another embodiment of the present invention, the prodrug component X may be represented as,

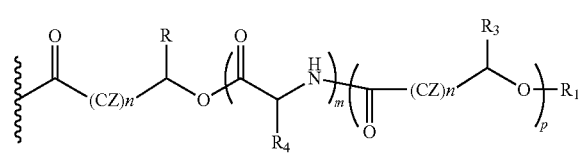

wherein,
CZ=CH2, or CHOR1;
R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and,
R and R3 can be same or different, and,
R and R3=Me, Ph, CH2COR2, or CHOR1COR2, where R2=OH or is an ester formed by the hydroxyl group of another alpha-hydroxy acid or is an amide formed by the amine group of an amino acid, and,
R4 is the side chain of a natural or non-natural amino acid, including side chains of (L)-isomers, (D)-isomers, mixtures of (L) and (D) isomers, racemates and mixtures of diastereomers, and,
m is an integer selected from 0 to 4, and,
n is an integer selected from 0 to 2, and,
p is an integer selected from 0 to 1.

In another embodiment of the present invention, the prodrug component X may be represented as,

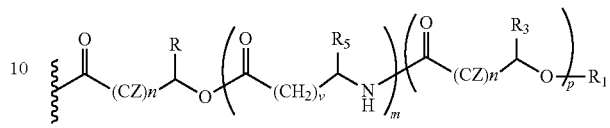

wherein,
CZ=CH2, or CHOR1;
R1=H, an acyl linkage of a fatty acid, an acyl linkage of an alpha-hydroxy acid, an acyl linkage of an amino acid, and an acyl linkage of a dicarboxylic acid including, but not limited to, fumaric acid, maleic acid and succinic acid, and,
R and R3 can be same or different, and,
R and R3=Me, Ph, CH2COR2, or CHOR1COR2, where R2=OH or is an ester formed by the hydroxyl group of another alpha-hydroxy acid or is an amide formed by the amine group of an amino acid, and,
R5=H, or COR2, where R2=OH or is an ester formed by the hydroxyl group of another alpha-hydroxy acid or is an amide formed by the amine group of an amino acid, or alkyl esters (O-alkyl, alkyl group is 1-4 carbon linear and branched, saturated and non-saturated alkyl groups), and,
the amino acids represented here depicts both natural and non-natural amino acids, the naturally occurring (L)-isomers, the non-natural (D)-isomers, mixtures of (L) and (D) isomers, racemates and mixtures of diastereomers, and,
m is an integer selected from 0 to 4, and,
n is an integer selected from 0 to 2, and,
p is an integer selected from 0 to 1, and,
v is an integer selected from 0 to 5.

In another embodiment of the present invention, the prodrug components X may be represented as,

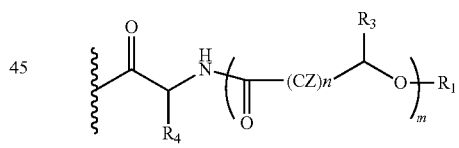

wherein,
CZ=CH2, or CHOR1;
R1=H, an acyl linkage of a fatty acid, an acyl linkage of an alpha-hydroxy acid, an acyl linkage of a amino acids or an acyl linkage of a dicarboxylic acid including, but not limited to, fumaric acid, maleic acid and succinic acid, and,
R3=Me, Ph, CH2COR2, or CHOR1COR2, where R2=OH or is an ester formed by the hydroxyl group of another alpha-hydroxy acid or is an amide formed by the amine group of an amino acid, and the amino acids represented here depicts both natural and non-natural amino acids, the naturally occurring (L)-isomers, the non-natural (D)-isomers, mixtures of (L) and (D) isomers, racemates and mixtures of diastereomers, and,
R4 is the side chain of a natural or non-natural amino acid, including side chains of (L)-isomers, (D)-isomers, mixtures of (L) and (D) isomers, racemates and mixtures of diastereomers, and, m is an integer selected from 0 to 4, and,
n is an integer selected from 0 to 2,
In another embodiment of the present invention, the prodrug component X may be represented as,

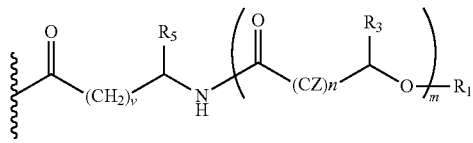

wherein,
CZ=CH2, or CHOR1;
R1=H, an acyl linkage of a fatty acid, an acyl linkage of an alpha-hydroxy acids, an acyl linkage of an amino acid, or an acyl linkage of a dicarboxylic acid including, but not limited to, fumaric acid, maleic acid and succinic acid, and,
R3=Me, Ph, CH2COR2, or CHOR1COR2, where R2=OH or is an ester formed by the hydroxyl group of another alpha-hydroxy acid or i an amide formed by the amine group of an amino acid, and the amino acids represented here depicts both natural and non-natural amino acids, the naturally occurring (L)-isomers, the non-natural (D)-isomers, mixtures of (L) and (D) isomers, racemates and mixtures of diastereomers, and,
R5=H, or COR2, where R2=OH or is an ester formed by the hydroxyl group of another alpha-hydroxy acid or is an amide formed by the amine group of an amino acid, or alkyl esters (O-alkyl, alkyl group is 1-4 carbon linear and branched, saturated and non-saturated alkyl groups), and,
the amino acids represented here depicts both natural and non-natural amino acids, the naturally occurring (L)-isomers, the non-natural (D)-isomers, mixtures of (L) and (D) isomers, racemates and mixtures of diastereomers, and,
m is an integer selected from 0 to 4, and,
n is an integer selected from 0 to 2, and,
v is an integer selected from 0 to 5.
In another embodiment of the present invention, the prodrug component X may be represented as,

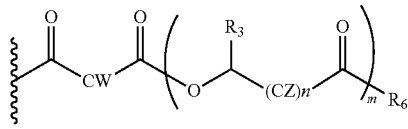

wherein,
CW=(CH2)q, or CH=CH (both E and Z isomers),
CZ=CH2, or CHOR1;
R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and,
R3=Me, Ph, CH2COR2, or CHOR1COR2, where R2=OH or is part of an ester formed by the hydroxyl group of another alpha-hydroxy acid or part of an amide formed by the amine group of an amino acid, and the amino acids represented here depicts both natural and non-natural amino acids, the naturally occurring (L)-isomers, the non-natural (D)-isomers, mixtures of (L) and (D) isomers, racemates and mixtures of diastereomers, and,
R6=OH or is f an ester formed by the hydroxyl group of another alpha-hydroxy acid or is an amide formed by the amine group of an amino acid, or alkyl esters (O-alkyl, alkyl group is 1-4 carbon linear and branched, saturated and non-saturated alkyl groups), and,
the amino acids represented here depicts both natural and non-natural amino acids, the naturally occurring (L)-isomers, the non-natural (D)-isomers, mixtures of (L) and (D) isomers, racemates and mixtures of diastereomers, and,
m is an integer selected from 0 to 4, and,
n is an integer selected from 0 to 2, and,
q is an integer selected from 2 to 6.
In another embodiment of the present invention, the prodrug component X may be represented as,

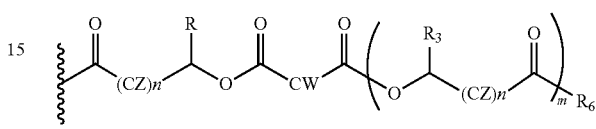

wherein,
CW=(CH2)q, or CH=CH (both E and Z isomers),
CZ=CH2, or CHOR1;
R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid, and,
R and R3 can be same or different, and,
R and R3=Me, Ph, CH2COR2, or CHOR1COR2, where R2=OH or is an ester formed by the hydroxyl group of another alpha-hydroxy acid or is an amide formed by the amine group of an amino acid, and the amino acids represented here depicts both natural and non-non-natural amino acids, the naturally occurring (L)-isomers, the non-natural (D)-isomers, mixtures of (L) and (D) isomers, racemates and mixtures of diastereomers, and,
R6=OH or is an ester formed by the hydroxyl group of another alpha-hydroxy acid or is an amide formed by the amine group of an amino acid, or alkyl esters (O-alkyl, alkyl group is 1-4 carbon linear and branched, saturated and non-non-saturated alkyl groups), and
the amino acids represented here depicts both natural and non-non-natural amino acids, the naturally occurring (L)-isomers, the non-natural (D)-isomers, mixtures of (L) and (D) isomers, racemates and mixtures of diastereomers, and,
m is an integer selected from 0 to 4, and,
n is an integer selected from 0 to 2, and,
q is an integer selected from 2 to 6.
In another embodiment of the present invention, the prodrug components X may be represented as,

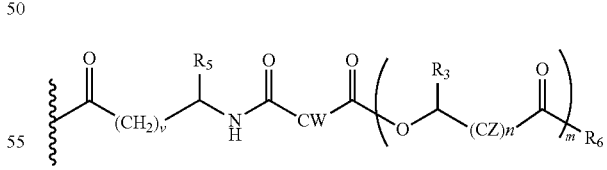

wherein,
CW=(CH2)q, or CH=CH, (both E and Z isomers), and,
R3=Me, Ph, CH2COR2, or CHOR1COR2, where R2=OH or is an ester formed by the hydroxyl group of another alpha-hydroxy acid or is an amide formed by the amine group of an amino acid, and the amino acids represented here depicts both natural and non-non-natural amino acids, the naturally occurring (L)-isomers, the non-natural (D)-isomers, mixtures of (L) and (D) isomers, racemates and mixtures of diastereomers, R5=H, COR2, where R2=OH or is part of an ester formed by the hydroxyl group of another alpha-hydroxy acid or part of an amide formed by the amine group of an amino acid, or alkyl esters (O-alkyl, alkyl group is 1-4 carbon linear and branched, saturated and non-non-saturated alkyl groups), and, R6=OH or is an ester formed by the alcohol (OH) part of another alpha-hydroxy acid or is an amide formed by the amine group of an amino acid, or alkyl esters (O-alkyl, alkyl group is 1-4 carbon linear and branched, saturated and non-non-saturated alkyl groups), and, m is an integer selected from 0 to 4, and,
n is an integer selected from 0 to 2, and,
q is an integer selected from 2 to 6, and,
v is an integer selected from 0 to 6.

In another embodiment of the present invention, the prodrug component X may be represented as,

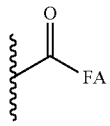

wherein,
FA is C8 to C20 saturated and unsaturated fatty acids including sorbic acid, stearic acid, oleic acid, palmitic acid, linoleic acid.

These fatty acids may be linear or branched chain acids, or a combination thereof; and in the case of unsaturated fatty acids, they may be cis- or trans-isomers (Z and E isomers).

With the ketone functional group present at the 6 positions of hydrocodone and hydromorphone, the ketone can be converted to its corresponding enolate and reacted with an activated prodrug side chain to form the corresponding prodrugs as the enolate ester. Upon prodrug cleavage, these prodrugs will revert back to the original opioid molecule with the keto group present intact.

In another embodiment of the present invention, with the hydroxyl functional group present at the 6 positions of morphine, codeine and dihydrocodeine, the hydroxyl group (—OH group) is reacted with an activated prodrug side chain to form the corresponding prodrugs of these molecules as its alcohol esters. Upon prodrug cleavage, these prodrugs will revert back to the original opioid molecules with the hydroxyl group (—OH group) present intact.

In another embodiment of the present invention, with the hydroxyl group present at the 17 position of buprenorphine, the hydroxyl group (—OH group) is reacted with an activated prodrug side chain to form the corresponding prodrug of buprenorphine. Upon prodrug cleavage, this prodrug will revert back to the original buprenorphine molecule with the hydroxyl group (—OH group) present intact.

The alpha-hydroxy carboxylic acid and its homo and hetero oligomers (with another alpha-hydroxy carboxylic acid) referred to in this invention should be understood to be covalently bound via a hydroxy group on the alpha-hydroxy carboxylic acid or on the oligomer to another carbonyl (originally part of a carboxyl group of another alpha-hydroxy carboxylic acid, or to another carbonyl of the carboxyl group of the amino acid, or to one carbonyl of the carboxyl group of a dicarboxylic acid (e.g., succinic acid, maleic acid, fumaric acid), while the carboxyl group from the initial alpha-hydroxy carboxylic acid is attached to the opioid.

If the initial carboxyl group that is attached to the opioid referred to in this invention is from an amino acid, it should be understood that the amino group of the said amino acid is to be bound via a covalent bond as the amide with the carboxyl group on the alpha-hydroxy carboxylic acid or the oligomer carbonyl (originally part of a carboxyl group of the alpha-hydroxy carboxylic acids) or to one carbonyl of the carboxyl group of a dicarboxylic acid (e.g., succinic acid, maleic acid, fumaric acid), or to one carbonyl of the carboxyl group of the fatty acids.

It should also be understood that if the initial carboxyl group that is attached to the opioid referred to in this invention is from alpha-hydroxy carboxylic acids and its homo and hetero oligomers (with another alpha-hydroxy carboxylic acid), the ensuing hydroxyl group may be capped as its ester by fatty acids.

It should also be understood that If the initial carboxyl group that is attached to the opioid referred to in this invention is from alpha-hydroxy carboxylic acids and its homo and hetero oligomers (with another alpha-hydroxy carboxylic acid), the ensuing hydroxyl group may be capped as its ester by dicarboxylic acids (e.g., succinic acid, maleic acid, fumaric acid).

In another embodiment of the present invention, when the covalently modified opioid is provided in oral dosage form (e.g., a tablet, capsule, caplet, liquid dispersion, etc.) it has increased resistance to manipulation. For instance, crushing of a tablet or disruption of a capsule does not substantially increase the rate and amount of opioid absorbed when compositions of the invention are ingested.

In another embodiment of the present invention, when the opioid covalently bound to the prodrug side chain is provided in oral dosage form: for example a tablet, capsule, caplet or other formulation that is resistant to generate opioid by physical manipulation such as crushing.

Another embodiment of the present invention provides opioid prodrug conjugates as a composition or method for treating pain in a patient (i.e., acute and chronic pain). It should be noted that different conjugates maybe be utilized to treat acute versus chronic pain.

Another embodiment of the present invention is a composition or method for a sustained-release opioid comprising a covalently bonded opioid conjugate, wherein said conjugate provides release of opioid at a rate where the level of opioid is within the therapeutic range, but below toxic levels, over an extended period of time (e.g., 8-24 hours or greater).

Another embodiment of the present invention is a composition or method for reducing variability in bioavailability, or preventing a toxic release of opioid, comprising opioid covalently bonded to the prodrug moiety, wherein said bound opioid maintains a steady-state plasma release curve, which provides therapeutically effective bioavailability but prevents spikes or sharp increases in blood concentrations compared to unbound opioid when given at doses exceeding those that are within the therapeutic range of opioid.

Another embodiment of the invention is a composition or method for preventing an extreme spike in plasma $C_{max}$ for opioid while still providing therapeutically effective bioavailability curve for opioid that has been covalently bonded to the prodrug moiety.

Another embodiment of the present invention is a method for reducing or preventing abuse related to the euphoric effect of a pharmaceutical opioid composition, comprising consuming said composition, wherein said composition comprises a prodrug moiety covalently attached to opioid, such that the pharmacological activity of opioid is substantially decreased when the composition is used in a manner inconsistent with approved instructions or in a manner that substantially increases the potential of overdose.

Other embodiments of the present invention are methods wherein said pharmaceutical composition is adapted solely for oral administration, and wherein said opioid is resistant to release from said prodrug moiety when the composition is administered parenterally (e.g., intranasally. Intravenously etc.). Preferably, said opioid would be preferentially released from said chemical moiety primarily in the presence of acid and/or enzymes present in the stomach or intestinal tract, respectively.

In another embodiment of the present invention, the covalently bonded opioid prodrug may also be in a pharmaceutically acceptable salt form. Pharmaceutically acceptable inorganic and organic acid addition salts are known in the art. Exemplary salts include, but are not limited to, hydrobromide, hydrochloride, hydroiodide, benzoate, bisulfate, tartrate, bitartrate, edetate, edisylate, estolate, esylate, ethanesulfonate, lactate, malate, maleate, mandelate, methanesulfonate, phosphate, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, borate, butyrate, calcium edetate, camphorate, camphorsulfonate, citrate, clavulariate, cyclopentanepropionate, digluconate, dodecylsulfate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydroxynaphthoate, isothionate, lactobionate, laurate, laurylsulphonate, mucate, naphthylate, napsylate, nicotinate, N-methylglucamine ammonium salt, oleate, palmitate, pamoate, pantothenate, pectinate, phosphateldiphosphate, pivalate, polygalacturonate, propionate, p-toluenesulfonate, saccharate, salicylate, stearate, subacetate, succinate, sulfate, sulfosaliculate, suramate, tannate, teoclate, tosylate, triethiodide, undecanoate, and valerate salts, and the like.

The term "amino acid" refers to one of twenty-two amino acids used for protein biosynthesis, as well as other amino acids that can be incorporated into proteins during translation. Such amino acids can be a natural amino acid, such as glycine, alanine, valine, leucine, isoleucine, aspartic acid, glutamic acid, serine, threonine, glutamine, asparagine, arginine, lysine, proline, phenylalanine, tyrosine, tryptophan, cysteine, methionine, histidine and beta alanine, or non-natural amino acids and alpha amino acids, beta amino acids, gamma amino acids, and epsilon amino acids (e.g., the amino group is remote relative to the carboxyl group).

The present invention also provides methods for providing, administering, prescribing, or consuming an opioid prodrug. The invention also provides pharmaceutical compositions comprising an opioid prodrug. The formulation of such a pharmaceutical composition can optionally enhance or achieve the desired release profile.

In a further embodiment of the present invention, non-limiting examples of opioid prodrugs of the present invention are shown in Formulae 1-90. In these formulae, it should be noted that while no salt forms have been depicted, all the formulae compounds can be prepared as their pharmaceutically acceptable salts, as previously described. In these formulae, it should also be noted that "OP" represent the opioid and the prodrug component —X, the ligand is chemically/covalently attached to the opioid "OP". In these formulae, it should also be noted that the opioids represented here include non-limiting examples of hydrocodone, hydromorphone, morphine, codeine, dihydrocodeine, and buprenorphine. The point of covalent attachment of the ligands to the opioids hydrocodone and hydromorphone is the $6^{th}$ position ketone enolate oxygen. For morphine, codeine, and dihydrocodeine it is the $6^{th}$ position hydroxyl group oxygen and for buprenorphine it is the $17^{th}$ position hydroxyl group oxygen.

Non-limiting examples of opioid prodrugs include the following compounds (formulae 1-90):

Formula 1

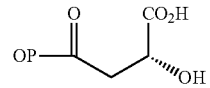

Formula 2

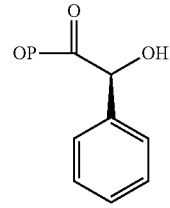

Formula 3

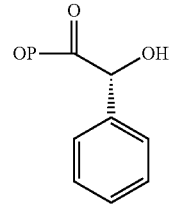

Formula 4

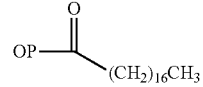

Formula 5

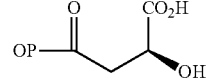

Formula 6

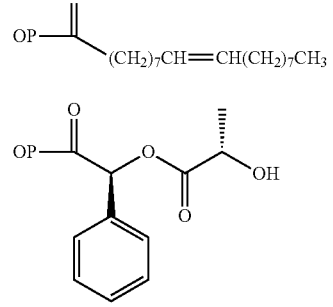

Formula 7

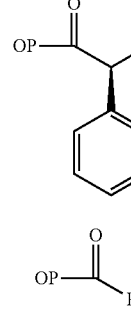

Formula 8

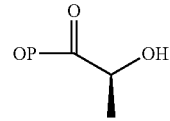

R = Palmitate
R = sorbate
R = $C_8$ to $C_{20}$ chain

Formula 9

-continued
Formula 10
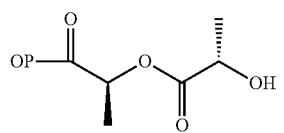
Formula 11
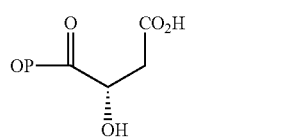
Formula 12
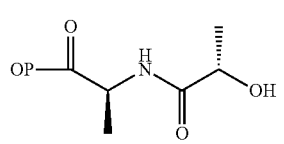
Formula 13
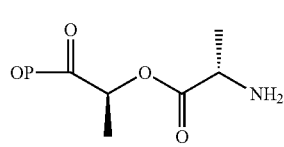
Formula 14
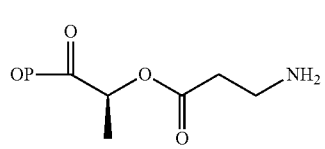
Formula 15
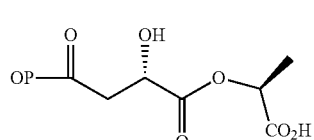
Formula 16
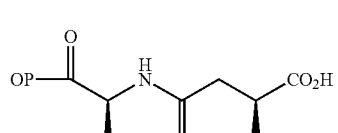
Formula 17
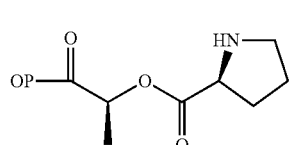
Formula 18
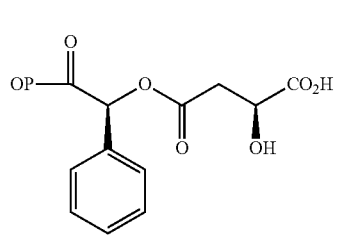
Formula 19
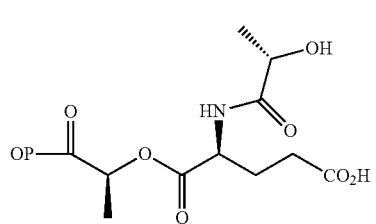
Formula 20
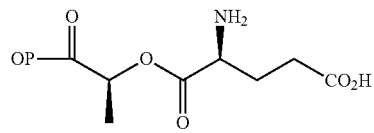
Formula 21
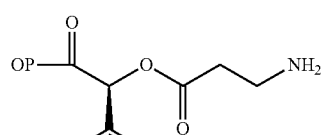
Formula 22
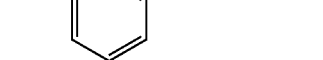
Formula 23
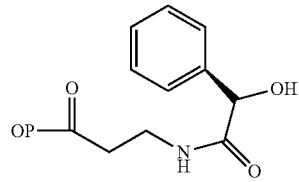
Formula 24
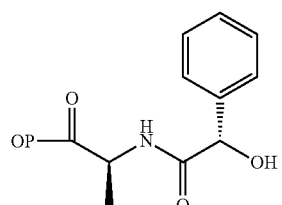
Formula 25
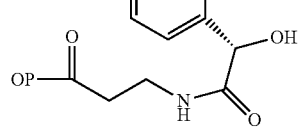
Formula 26
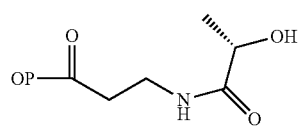
Formula 27
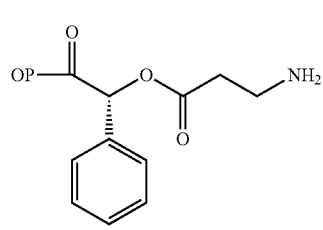

Formula 28, Formula 29, Formula 30, Formula 31, Formula 32, Formula 33, Formula 34, Formula 35, Formula 36, Formula 37, Formula 38, Formula 39, Formula 40, Formula 41, Formula 42, Formula 43, Formula 44

Formula 45
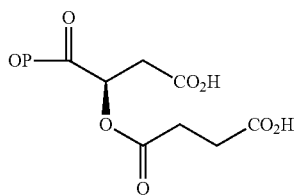
Formula 46
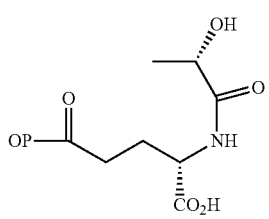
Formula 47
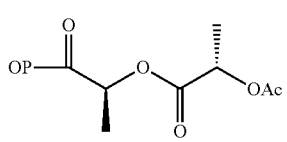
Formula 48
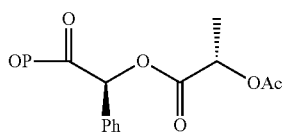
Formula 49
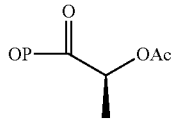
Formula 50
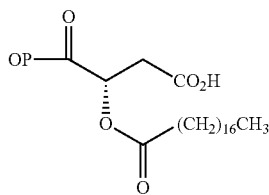
Formula 51
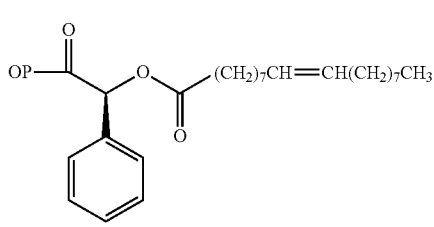
Formula 52
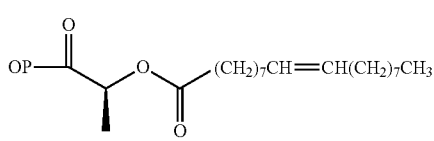
Formula 53
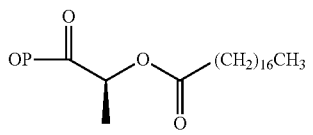
Formula 54
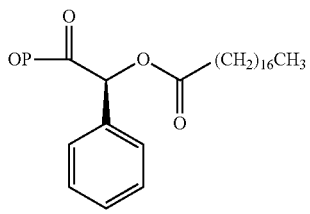
Formula 55
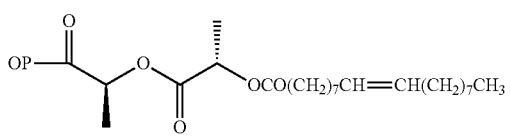
Formula 56
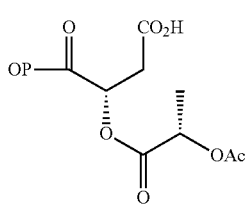
Formula 57
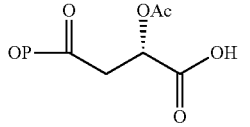
Formula 58
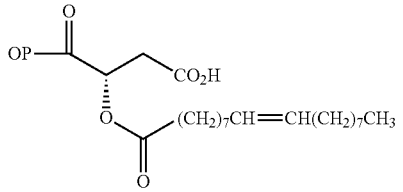
Formula 59
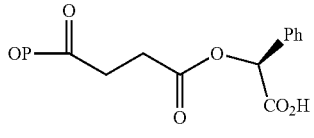
Formula 60
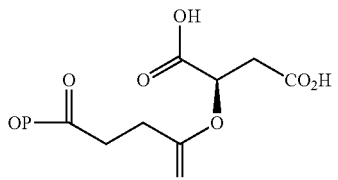
Formula 61
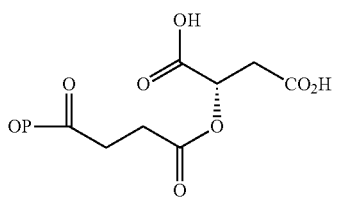

-continued
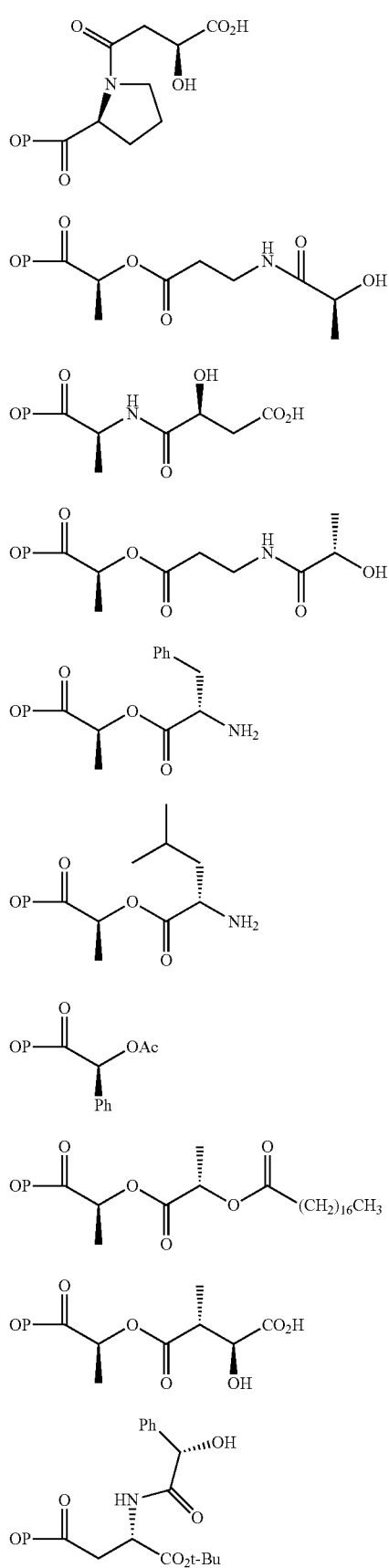
Formula 62
Formula 63
Formula 64
Formula 65
Formula 66
Formula 67
Formula 68
Formula 69
Formula 70
Formula 71
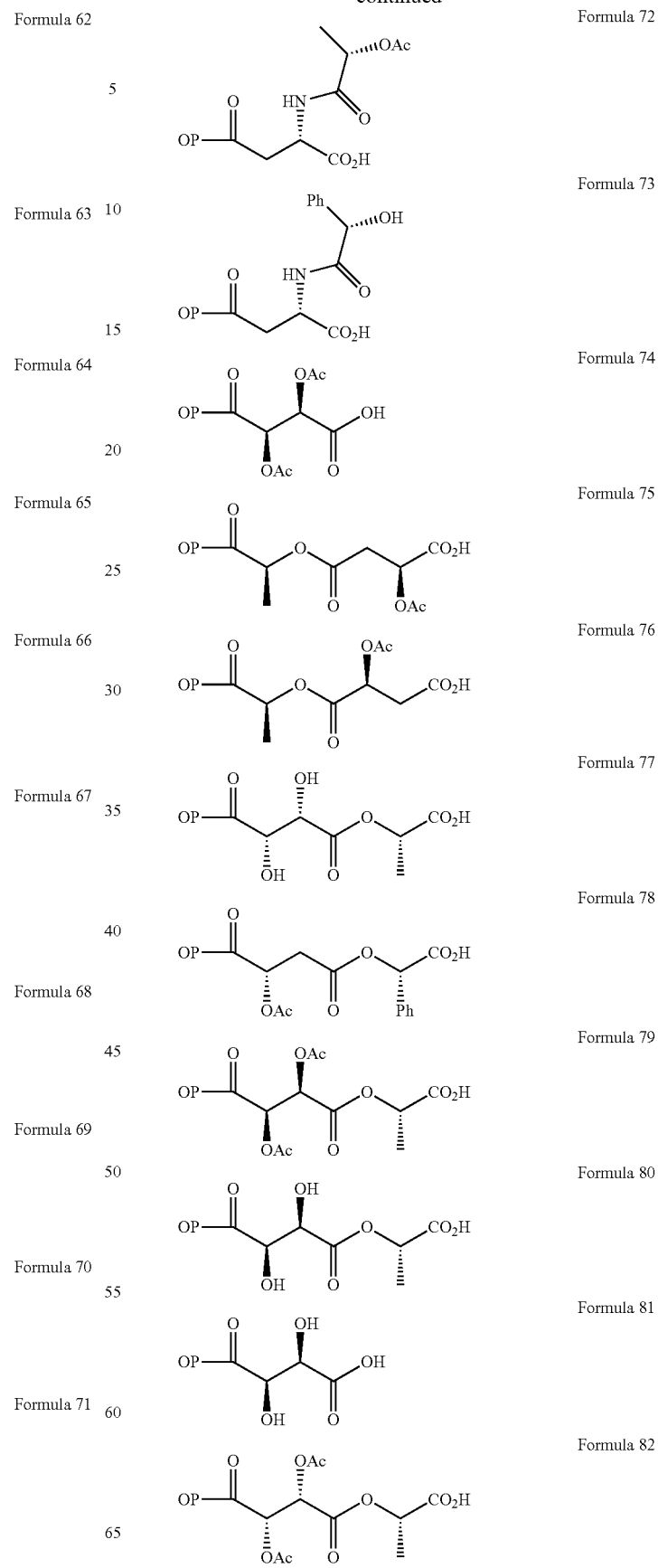
Formula 72
Formula 73
Formula 74
Formula 75
Formula 76
Formula 77
Formula 78
Formula 79
Formula 80
Formula 81
Formula 82

27

-continued

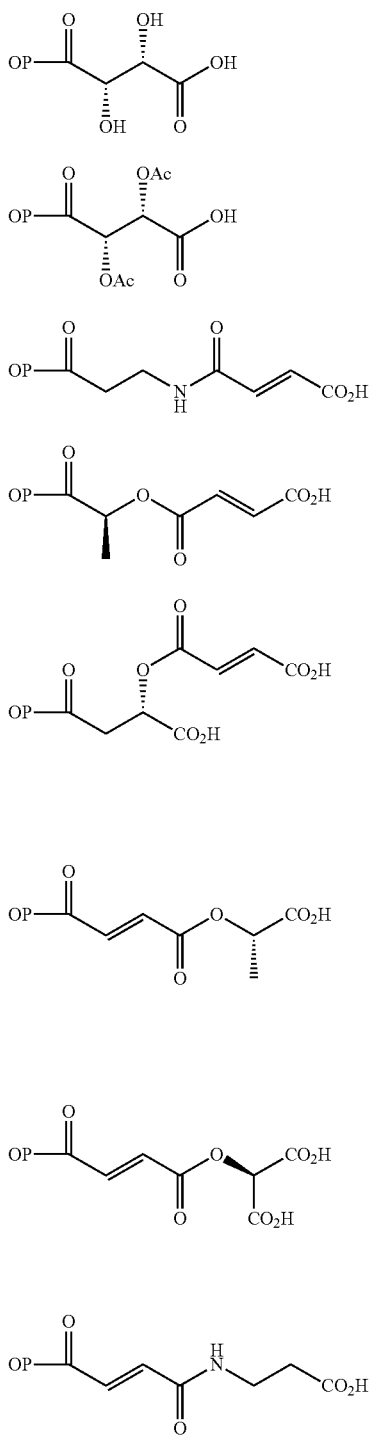

Formula 83

Formula 84

Formula 85

Formula 86

Formula 87

Formula 88

Formula 89

Formula 90

EXAMPLES

Processes for Preparing Opioid Conjugates

Two general procedures have been used for the preparation of various opioid prodrug conjugates OP—X, and more specifically:

28

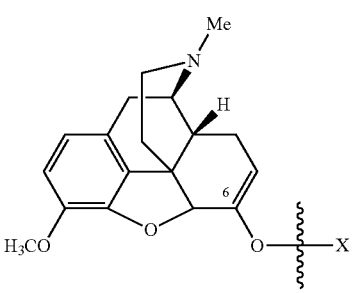

Hydrocodone prodrug

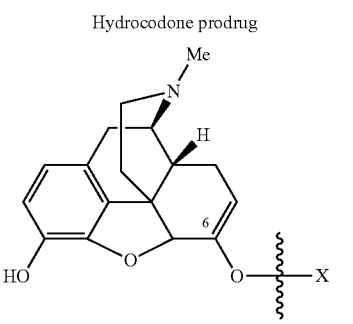

Hydromorphone prodrug

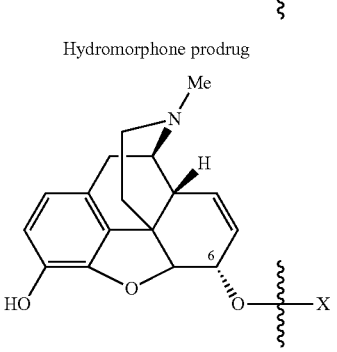

Morphine prodrug

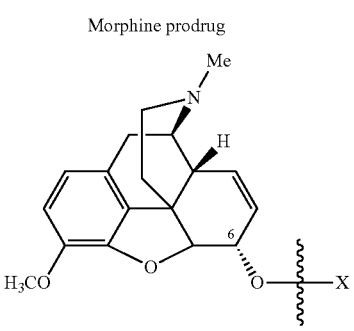

Codeine prodrug

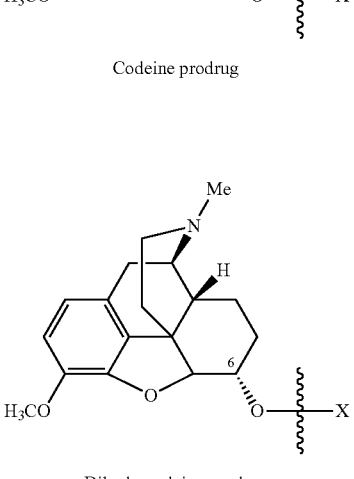

Dihydrocodeine prodrug

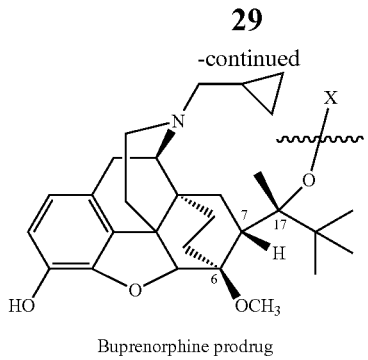

Buprenorphine prodrug

The procedure involves treating opioid first with a base followed by reaction with the carboxyl-activated prodrug moieties. In the case of phenolic opioids (e.g., hydroxymorphone, morphine, buprenorphine), the phenolic —OH group of the starting material opioid is protected with Boc.

General Procedure 1—Opioid Coupling with the Activated Prodrug Side Chain (KO$^t$Bu Procedure)

To a solution of opioid (1.05 g, 3.2 mmol) in THF (10 mL) is added KO$^t$Bu (1M solution in THF, 1.05 eq.) at 0° C., then stirred at ambient temperature for 30 min. The brown solution is cooled down to −78° C. and a solution of Boc-hydroxyl protected Osu-active ester of alpha-hydroxy acid (1.05 g, 3.4 mmol) in THF (20 mL) is added over a period of 5 mins. After stirring the reaction at −78° C. for 30 minutes, it is allowed to warm to RT over a period of 3 hrs. The turbid reaction mixture is poured into saturated (satd) NH$_4$Cl solution (150 mL), stirred for 5 mins and extracted with EtOAc (250 mL). The organic part is washed with aqueous (aq) NH$_4$Cl, aq. NaHCO$_3$, brine, dried over Na$_2$SO$_4$ and evaporated to dryness to give the product (1.5 g, purity 96.5%).

In some cases the crude product may require further purification by standard column chromatography. The product may be further characterized by nuclear magnetic resonance (NMR) spectroscopy, mass spectroscopy (MS), and elemental analysis.

General Procedure 2—Opioid Coupling with the Activated Prodrug Side Chain (LHMDS [Lithium Hexamethyl Disilaside] Procedure)

To a solution of opioid (1.05 g, 3.2 mmol) in THF (10 mL) is added LHMDS (LiN(TMS)$_2$) (1M solution in THF, 1.05 eq.) at 0° C., then stirred at ambient temperature for 30 min. The brown solution is cooled down to −78° C. and a solution of Boc-hydroxyl protected Osu-active ester of alpha-hydroxy acid (1.05 g, 3.4 mmol) in THF (20 mL) is added over a period of 5 mins. After stirring the reaction at −78° C. for 30 minutes, it is allowed to warm to room temperature (RT) over a period of 3 hrs. The turbid reaction mixture is poured into satd NH$_4$Cl solution (150 mL), stirred for 5 mins and extracted with EtOAc (250 mL). The organic part is washed with aqueous (aq) NH$_4$Cl, aq. NaHCO$_3$, brine, dried over Na$_2$SO$_4$, and evaporated to dryness to yield the product (1.4 g, purity 95%).

In some cases the crude product may require further purification by standard column chromatography. The product may be further characterized by NMR, MS and elemental analysis.

Boc Group Deprotection from the Coupled Enol-Ester Prodrug or Alcohol-Ester Product Boc group protection is used to protect the hydroxyl group(s) of the alpha-hydroxy carboxylic acids. After the oxycodone coupling, the Boc group is removed by the following general procedure. To a solution of the hydroxyl Boc-protected coupled product (1.5 g) in IPAc (15 mL) is added 4N HCl/dioxane (15 mL) and the reaction mixture is stirred at RT for 3 h (white ppt formation takes place after 10-15 mins). The solution is diluted with IPAc 50 mL), stirred for 10 mins. The precipitate is filtered, washed with IPAc and dried to give the deprotected product (quantitative yield). In this case the product is isolated as the HCl salt. HPLC purity ~95%. The product may be further characterized by NMR, MS and elemental analysis.

Boc Group Deprotection from the Coupled Enol-Ester Prodrug Product (Alternative General Procedure)

A third general procedure may also be used to remove the Boc group from the coupled enol-ester prodrug product. To a solution of the above, hydroxyl Boc-protected coupled product (1.5 g) in dichloromethane (15 mL) was added trifluoro acetic acid (15 mL) and the reaction mixture was stirred at RT for 3 hrs. The reaction mixture was concentrated to a dry powder on a rotavap and the residue was further purified by either trituration or chromatography as a TFA salt of the enol ester prodrug product. In this case the product is isolated as the TFA salt. HPLC purity ~95%. The product was further characterized by NMR, MS and elemental analysis.

Synthesis of the Activated Side Chain—OSu Ester for Opioid Coupling

Generally, N-hydroxy succinimide ester activated carboxylic acid of the alpha-hydroxy carboxylic acid is used for oxycodone coupling. To a solution of the hydroxyl Boc-protected alpha-hydroxy carboxylic acid (1 g, 1.1 mmol) and NHS (N-hydroxy succinimide) (1.05 eq) in THF (10 mL) is added a solution of DCC (1.05 eq) in THF (5 mL) at 0° C. The reaction mixture is slowly brought to RT and left overnight at RT. The turbid solution is filtered and the filtrate is used as such for the next step coupling process.

Depending on the specific stability of the compound being synthesized, the —OSu ester also can be precipitated and crystallized.

EMBODIMENTS

Various embodiments are listed below. It will be understood that the embodiments listed below may be combined with all aspects and other embodiments in accordance with the scope of the invention.

Embodiment 1

Opiod prodrugs of the following formulae where the prodrug moiety X is attached covalently to the opioid molecules,

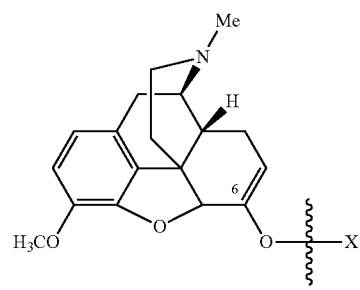

Hydrocodone prodrug

-continued

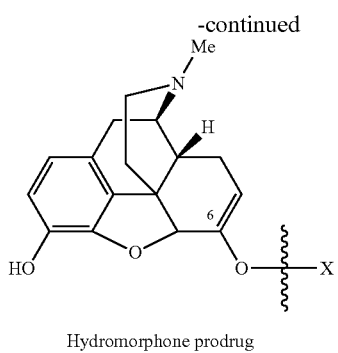

Hydromorphone prodrug

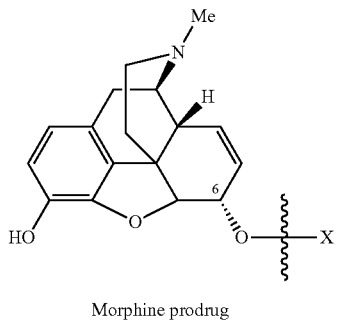

Morphine prodrug

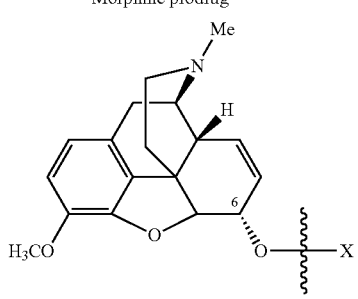

Codeine prodrug

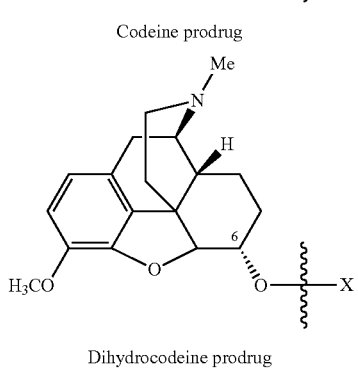

Dihydrocodeine prodrug

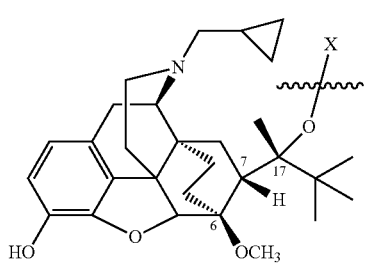

Buprenorphine prodrug or a pharmaceutically acceptable salt thereof.

Embodiment 2

Opioid prodrugs of embodiment 1 wherein the opioids are Hydrocodone, hydromorphone, morphine, codeine, dihydrocodeine, or buprenorphine.

Embodiment 3

Opioid prodrugs of embodiment 1 or 2 wherein the prodrug moiety X is chemically/covalently attached to hydrocodone and hydromorphone at their $6^{th}$ position oxygen atoms as its ketone enolate esters respectively.

Embodiment 4

Opioid prodrugs of embodiment 1 or 2 wherein the prodrug moiety X is chemically/covalently attached to morphine, codeine and dihydrocodeine at their $6^{th}$ position oxygen atoms as their alcohol esters respectively.

Embodiment 5

Opioid prodrugs of embodiment 1 or 2 wherein the prodrug moiety X is chemically/covalently attached to buprenorphine at its $17^{th}$ position oxygen atoms as its alcohol ester.

Embodiment 6

The opioid prodrugs of embodiments 1 or 2, wherein X is a prodrug moiety ligand selected from alpha-hydroxy carboxylic acid and derivatives as monomers, alpha-hydroxy carboxylic acid homo-oligomers, alpha-hydroxy carboxylic acid hetero oligomers with another alpha-hydroxy carboxylic acid, alpha-hydroxy carboxylic acid hetero oligomers with amino acids, alpha-hydroxy carboxylic acid hetero oligomers with dicarboxylic acids, alpha-hydroxy carboxylic acid hetero oligomers with fatty acids, fatty acids, and other GRAS-based reagents.

Embodiment 7

The opioid prodrugs of embodiment 6 wherein homo- and hetero-'mers' include both linear and branched 'mers'. The homo- and hetero-'mers' may also be cross linked with other GRAS reagents such as alpha-hydroxy carboxylic acids and amino acids.

Embodiment 8

The opioid prodrugs of embodiment 6 wherein the alpha-hydroxy carboxylic acid is selected from lactic acid, tartaric acid, malic acid, citric acid, mandelic acid, pantoic acid, pantothenic acid, 2-hydroxy glutaric acid, 3-hydroxy glutaric acid, and other poly-hydroxy carboxylic acids derived from sugars and carbohydrates. The naturally occurring (L)-isomers, the non-natural (D)-isomers, varying mixtures of (L) and (D) isomers, racemates and mixtures of diastereomers, and meso-isomers are all included in the term "alpha-hydroxy carboxylic acid".

Embodiment 9

The opioid prodrugs of embodiment 6 wherein the amino acids represented here include both natural (all 22 of the proteinogenic amino acids), and non-natural amino acids, the naturally occurring (L)-isomers, the non-natural (D)- isomers, varying mixtures of (L) and (D) isomers, racemates and mixtures of diastereomers. The amino acids represented here also include alpha amino acids, beta amino acids, gamma amino acids, and epsilon amino acids (amino group remote relative to the carboxyl group).

Embodiment 10

The opioid prodrugs of embodiment 6 wherein the fatty acids represented here include long chain carboxylic acids, ranging in lengths between eight carbons (C8) to twenty carbons (C20), and said fatty acids may be linear or branched chains, and include both saturated and non-nonsaturated chains, and in the case of unsaturated fatty acids include both cis- and trans-isomers (Z and E isomers), wherein examples of such fatty acids include, but are not limited to, sorbic acid, stearic acid, oleic acid, palmitic acid, and linoleic acid.

Embodiment 11

The opioid prodrugs of embodiment 6 wherein the dicarboxylic acids represented here to make hetero oligomers with alpha-hydroxy carboxylic acid include, but are not limited to, fumaric acid, maleic acid, and succinic acid.

Embodiment 12

The opioid prodrugs of embodiment 1 or 2, wherein ligand X is further represented as X is equal to ligands 1-16 (shown below);

Ligand 1
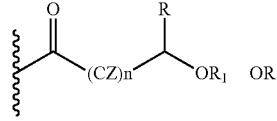

Ligand 2
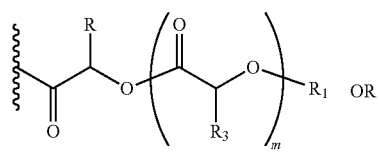

Ligand 3
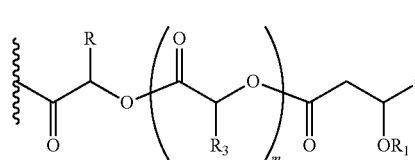

Ligand 4
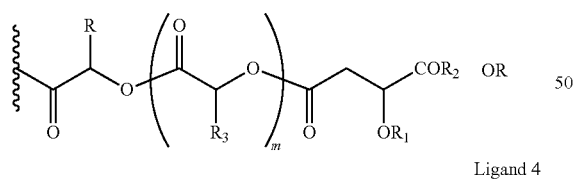

Ligand 5
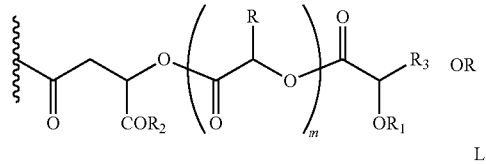

Ligand 6
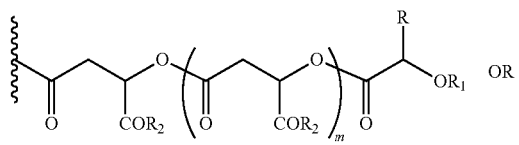

Ligand 7
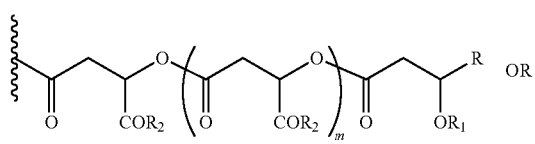

Ligand 8
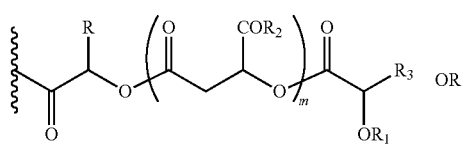

Ligand 9
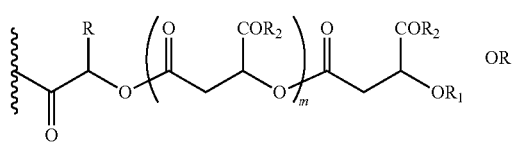

Ligand 10
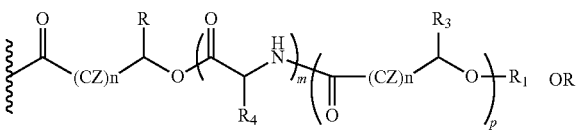

Ligand 11
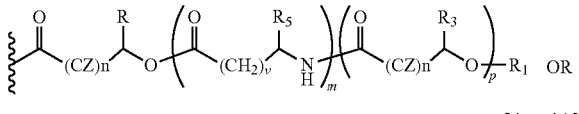

Ligand 12
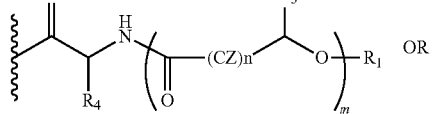

Ligand 13
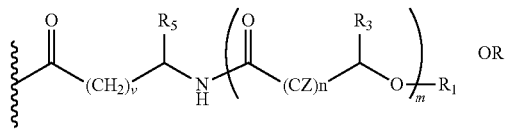

Ligand 14
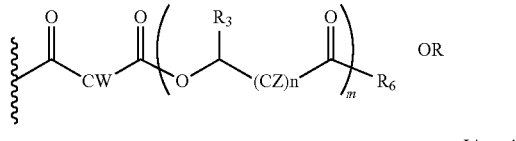

Ligand 15
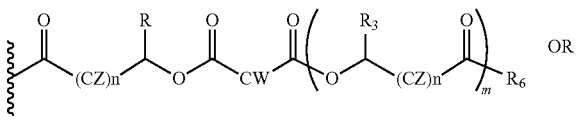

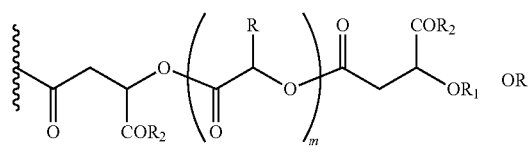

Ligand 16

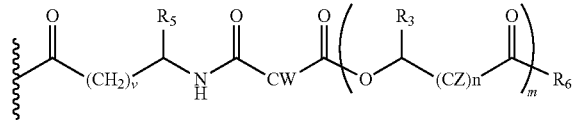

Wherein,
in ligands 1-16,
CZ=CH2, or CHOR1,
R1=H, an acyl linkage of a fatty acid, an acyl linkage of an alpha-hydroxy acid, an acyl linkage of an amino acid, or an acyl linkage of a dicarboxylic acid including, but not limited to, fumaric acid, maleic acid and succinic acid,
R=Me, Ph, CH2COR2, CHOR1COR2, or COR2 (when n is not zero),
R2=OH, or is an ester formed by the hydroxyl group of another alpha-hydroxy acid or is an amide formed by the amine group of an amino acid, and the amino acids represented here depicts both natural and non-non-natural amino acids, the naturally occurring (L)-isomers, the non-natural (D)-isomers, mixtures of (L) and (D) isomers, racemates and mixtures of diastereomers, or O-alkyl (alkyl esters, where the alkyl group is 1-4 carbon linear and branched, saturated and non-saturated alkyl groups),
R3=Me, Ph, CH2COR2, CHOR1COR2, or COR2 (when n is not zero),
R4 is the side chain of a natural or non-natural amino acid, including side chains of (L)-isomers, (D)-isomers, mixtures of (L) and (D) isomers, racemates and mixtures of diastereomers (R4 in ligands 10 and 12),
R5=H, or COR2,
CW=(CH2)q, or CH=CH (both E and Z isomers),
R6=OH or is an ester formed by the hydroxyl group of another alpha-hydroxy acid or is an amide formed by the amine group of an amino acid, or alkyl esters, and the amino acids represented here depicts both natural and non-natural amino acids, the naturally occurring (L)-isomers, the non-natural (D)-isomers, mixtures of (L) and (D) isomers, racemates and mixtures of diastereomers, or R6 is an ester with an alkyl group (O-alkyl, alkyl group is 1-4 carbon linear and branched, saturated and non-saturated alkyl groups),
and m is an integer selected from 0 to 4, and n is an integer selected from 0 to 2, and q is an integer selected from 2 to 6, and v is an integer selected from 0 to 6

Embodiment 13

The opioid prodrugs of embodiment 1 or 2, wherein X is a prodrug moiety and is represented by ligand 17;

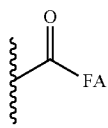

ligand 17

Wherein,
FA is C8 to C20 saturated fatty acids, C8 to C20 unsaturated fatty acids, including but not limited to, sorbic acid, stearic acid, oleic acid, palmitic acid, linoleic acid. These fatty acids could be both linear and branched chain fatty acids, and in the case of unsaturated fatty acids both cis- and trans-isomers (Z and E isomers) are included.

Embodiment 14

Opioid prodrug compounds represented by any one of formulae 1-90.

Embodiment 15

A composition comprising the compound of any of embodiments 1-13.

Embodiment 16

The compound of embodiment 14 wherein the compound, or a pharmaceutically acceptable salt thereof, maintains a steady-state release curve in blood that provides therapeutically effective opioid bioavailability.

Embodiment 17

The composition of embodiment 15, wherein when said composition is administered orally and the bioavailability of opioid is maintained.

Embodiment 18

A method of treating pain comprising orally administering the composition of embodiment 15 to a patient.

Embodiment 19

The composition of embodiment 14, wherein the said composition comprises a pharmaceutically acceptable salt form of the opioid prodrug compound.

Embodiment 20

A pharmaceutical composition comprising one or more of the opioid prodrugs of embodiment 14 and one or more pharmaceutically acceptable excipients.

What is claimed:
1. An opioid prodrug of any of the following formulae where the prodrug moiety X is attached covalently to the opioid molecule,

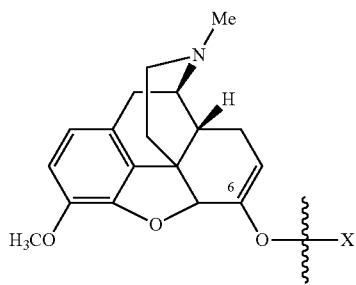

Hydrocodone prodrug

-continued

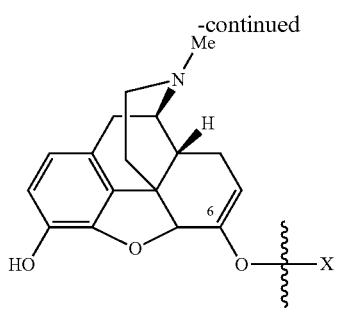

Hydromorphone prodrug

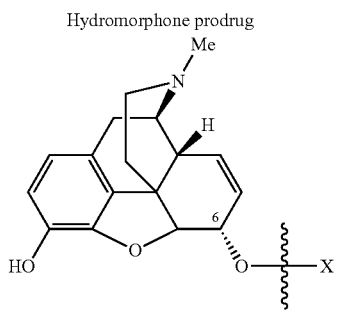

Morphine prodrug

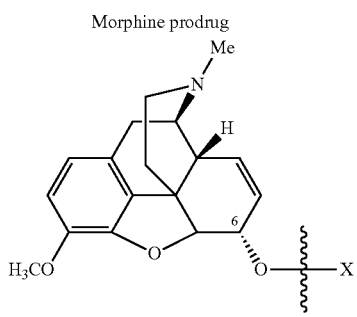

Codeine prodrug

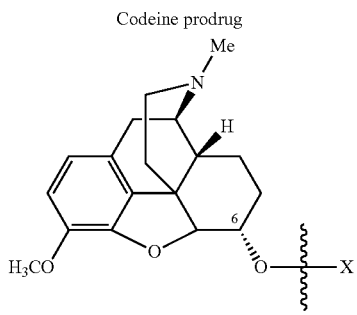

Dihydrocodeine prodrug

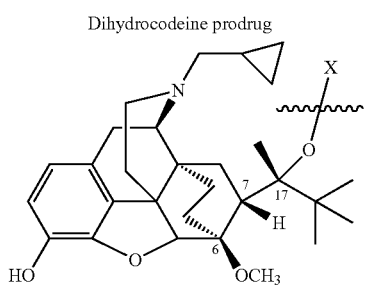

Buprenorphine prodrug or a pharmaceutically acceptable salt thereof,
wherein X is an alpha-hydroxy carboxylic acid selected from the group consisting of lactic acid, tartaric acid, malic acid, citric acid, mandelic acid, pantoic acid, panthothenic, 2-hydroxy glutaric acid, 3-hydroxy glutaric acid, and other poly-hydroxy carboxylic acids derived from sugars and carbohydrates.

2. The opioid prodrug of claim 1 wherein the opioid is hydrocodone, hydromorphone, morphine, codeine, dihydrocodeine, or buprenorphine.

3. The opioid prodrug of claim 2 wherein the prodrug moiety X is chemically/covalently attached to hydrocodone or hydromorphone at their $6^{th}$ position oxygen atoms as a ketone enolate ester.

4. An opioid prodrug compound of formula

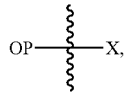

wherein OP comprises an opioid selected from the group consisting of hydrocodone, hydromorphone, morphine, codeine, dihydrocodeine, and buprenorphine, X comprises a prodrug covalently attached to the opioid, and

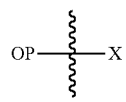

is selected from the group consisting of

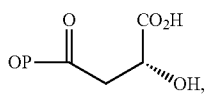
Formula 1

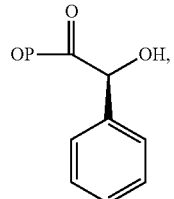
Formula 2

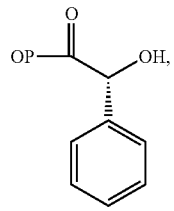
Formula 3

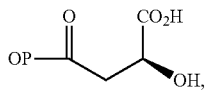
Formula 5

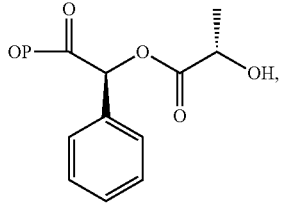
Formula 7

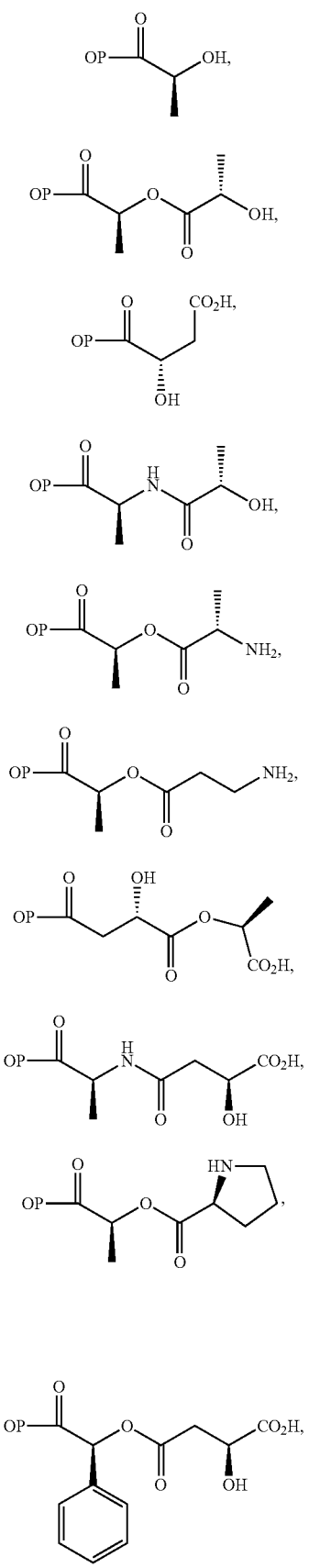
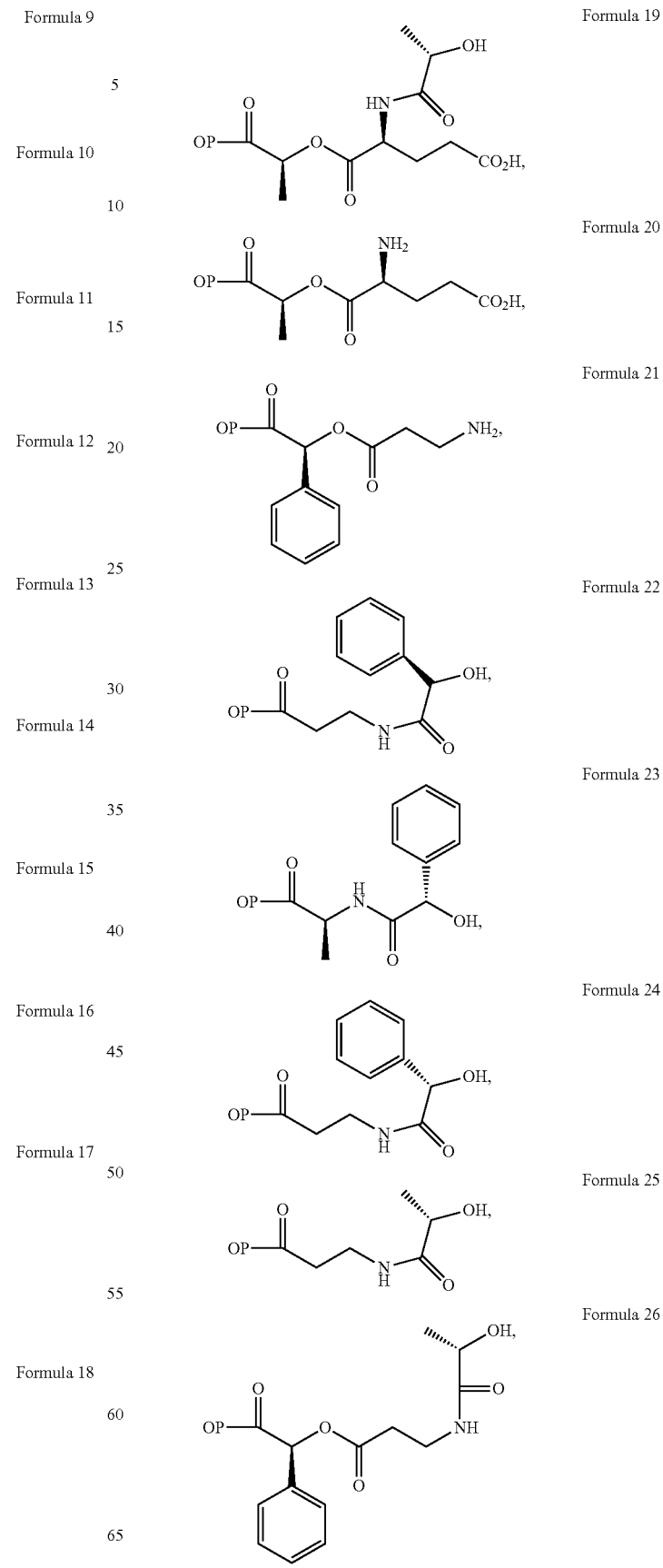

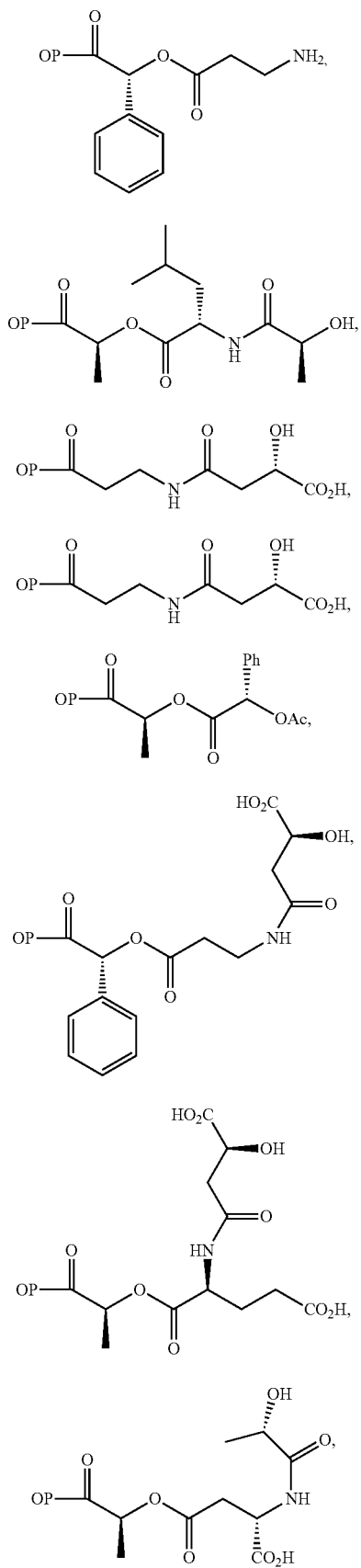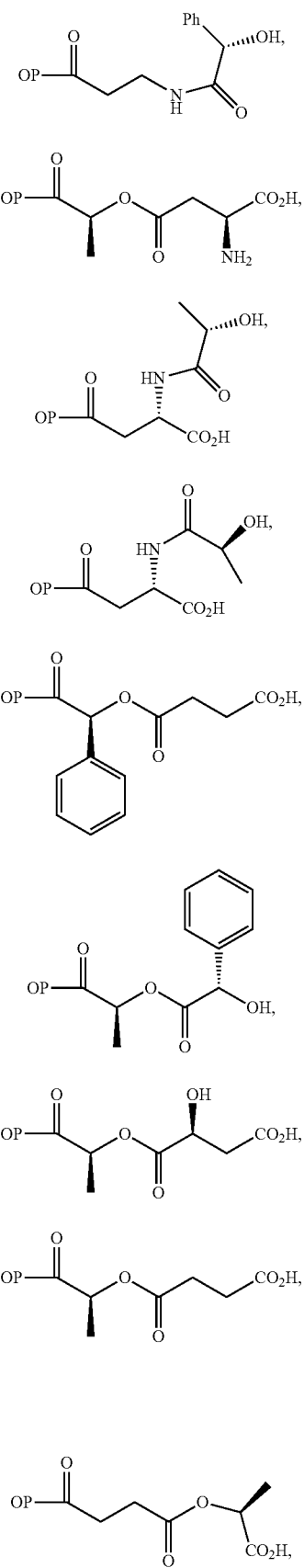

Formula 45
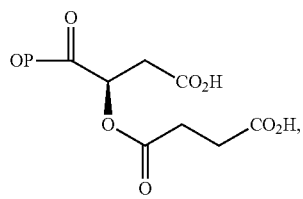
Formula 46
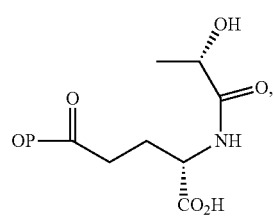
Formula 47
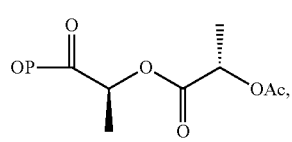
Formula 48
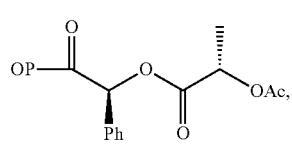
Formula 49
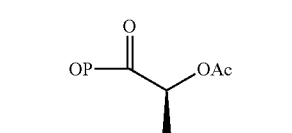
Formula 50
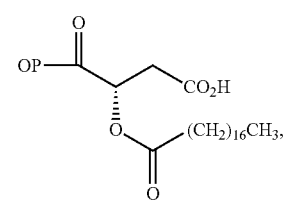
Formula 51
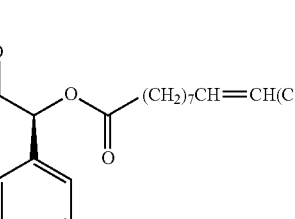
Formula 52
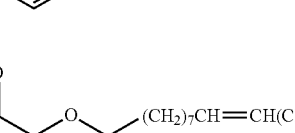
Formula 53
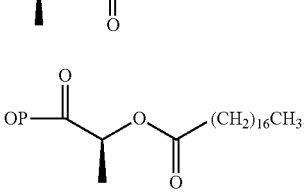
Formula 54
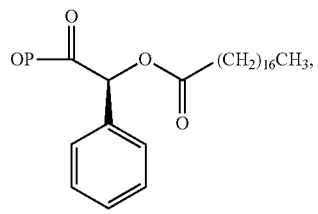
Formula 55
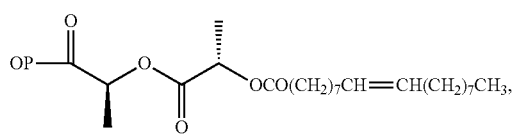
Formula 56
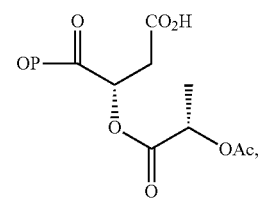
Formula 57
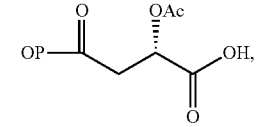
Formula 58
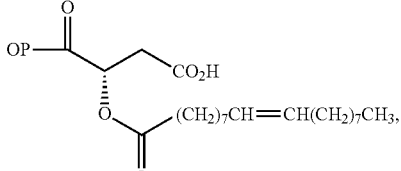
Formula 59
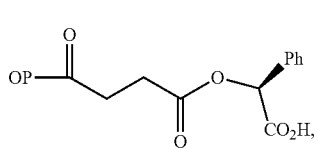
Formula 60
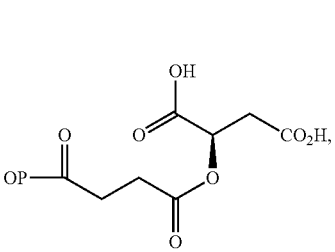
Formula 61
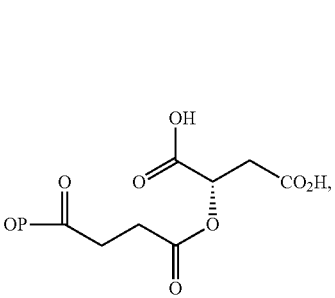

-continued
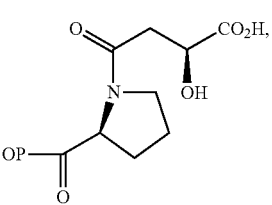
Formula 62
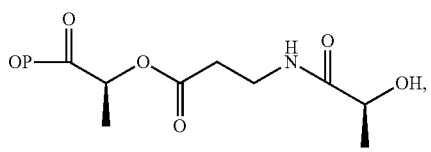
Formula 63
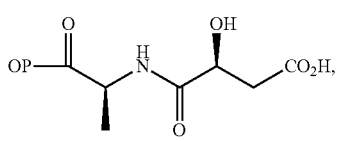
Formula 64
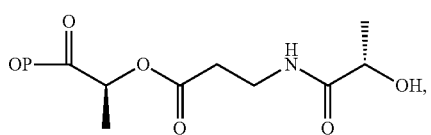
Formula 65
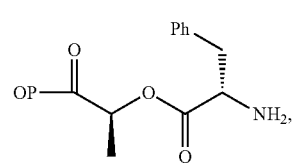
Formula 66
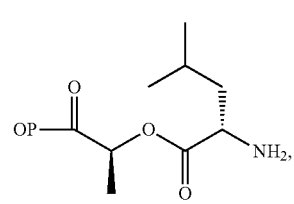
Formula 67
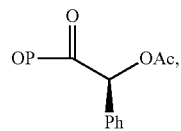
Formula 68
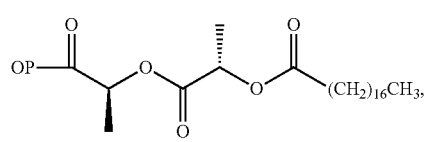
Formula 69
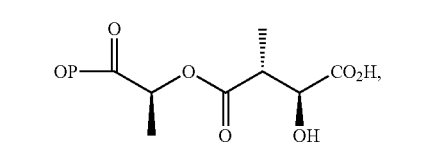
Formula 70
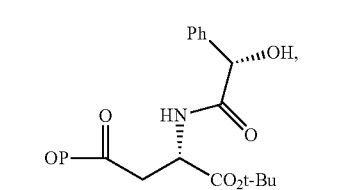
Formula 71
-continued
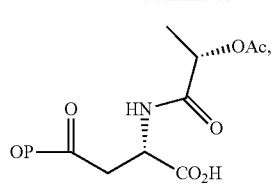
Formula 72
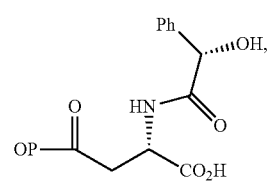
Formula 73
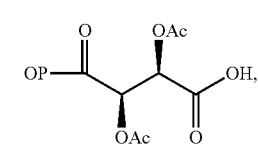
Formula 74
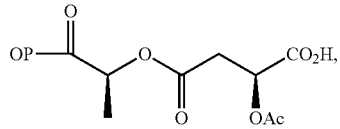
Formula 75
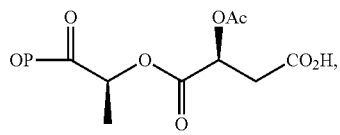
Formula 76
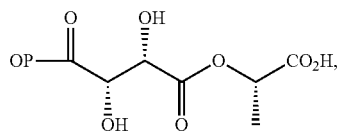
Formula 77
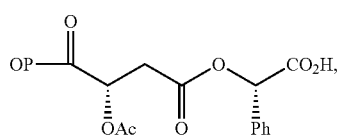
Formula 78
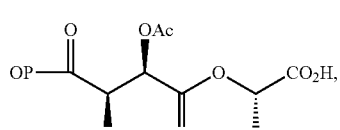
Formula 79
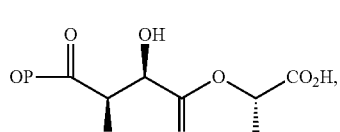
Formula 80
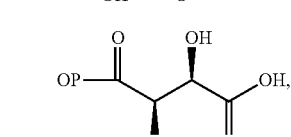
Formula 81
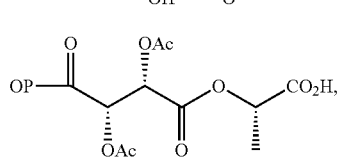
Formula 82

-continued

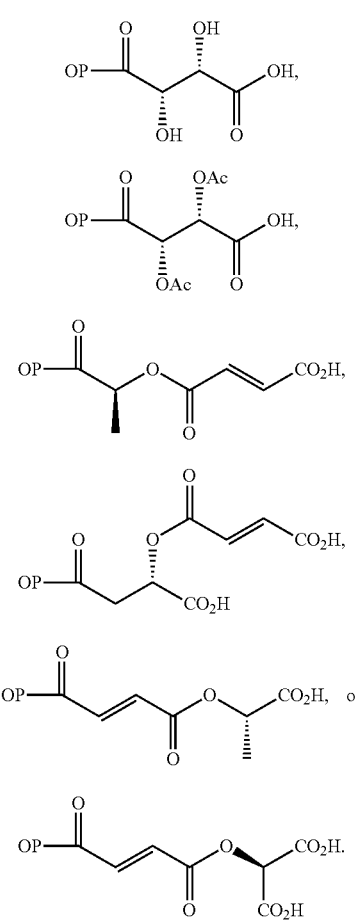

Formula 83

Formula 84

Formula 86

Formula 87

Formula 88

Formula 89

5. A pharmaceutical composition comprising one or more of the opioid prodrugs according to claim 4 and one or more pharmaceutically acceptable excipient.

6. An oral pharmaceutical composition comprising the compound of claim 1 and a pharmaceutically acceptable excipient.

7. The pharmaceutical composition of claim 4, wherein the compound is a pharmaceutically acceptable salt form.

8. A method of treating pain comprising orally administering the composition of claim 6 to a patient.

9. The opioid prodrug of claim 1, wherein X is malic acid.

10. The opioid prodrug of claim 1, wherein the opioid is hydrocodone.

11. The opioid prodrug of claim 1, wherein X is malic acid and the opioid is hydrocodone.

12. The opioid prodrug compound of claim 4, wherein the opioid prodrug compound of formula

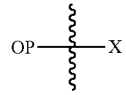

is represented by any one of formulae

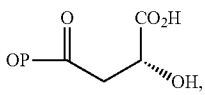
Formula 1

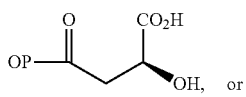
Formula 5

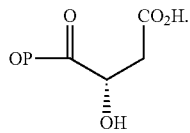
Formula 11

* * * * *